US012667433B2

(12) United States Patent
Deboeuf et al.

(10) Patent No.: US 12,667,433 B2
(45) Date of Patent: Jun. 30, 2026

(54) ROBOTIZED MODULE FOR GUIDING AN ELONGATE FLEXIBLE MEDICAL DEVICE

(71) Applicant: ROBOCATH, Rouen (FR)

(72) Inventors: Sébastien Deboeuf, Sotteville-les-Rouen (FR); Bruno Fournier, Saint Ouen (FR); Jacques Marignier, Le Mesnil Esnard (FR); Ines Ouali, Marseilles (FR); Philippe Bencteux, Saint Martin du Vivier (FR); Fabien Destrebecq, Bourgtheroulde (FR)

(73) Assignee: ROBOCATH, Rouen (FR)

( * ) Notice: Subject to any disclaimer, the term of this patent is extended or adjusted under 35 U.S.C. 154(b) by 1087 days.

(21) Appl. No.: 15/318,145

(22) PCT Filed: Jun. 12, 2015

(86) PCT No.: PCT/FR2015/051566

§ 371 (c)(1),
(2) Date: Dec. 12, 2016

(87) PCT Pub. No.: WO2015/189531

PCT Pub. Date: Dec. 17, 2015

(65) Prior Publication Data

US 2022/0061933 A1 Mar. 3, 2022

(30) Foreign Application Priority Data

Jun. 12, 2014 (FR) ...................................... 14 55330

(51) Int. Cl.
*A61M 25/01* (2006.01)
*A61B 34/00* (2016.01)
(Continued)

(52) U.S. Cl.
CPC .............. *A61B 34/30* (2016.02); *A61B 34/25* (2016.02); *A61B 34/32* (2016.02); *A61B 46/10* (2016.02);
(Continued)

(58) Field of Classification Search
None
See application file for complete search history.

(56) References Cited

U.S. PATENT DOCUMENTS 6,096,004 A † 8/2000 Meglan
2007/0185464 A1 8/2007 Hauck
(Continued)

FOREIGN PATENT DOCUMENTS

EP 2567670 A1 3/2013
WO 2007008967 A2 † 1/2007
WO WO-2008/115151 A1 9/2008

OTHER PUBLICATIONS

International Search Report Application No. PCT/FR2015/051566; mailed on Mar. 30, 2016.

*Primary Examiner* — Tse W Chen
*Assistant Examiner* — Martin Nathan Ortega

(57) ABSTRACT

The robotized module for actuating an elongated flexible medical device comprises a pair of actuation members that are either in an actuation configuration or in a free configuration. The pair of actuation members is movable between a first position and a second position. A control member acts in repeated cyclical manner to cause the actuation member, when in the actuation configuration, to move from the first position to the second position, and when in the free configuration, to move from the second position to the first position.

27 Claims, 26 Drawing Sheets

(51) Int. Cl.

| | | |
|---|---|---|
| *A61B 34/30* | (2016.01) | |
| *A61B 34/32* | (2016.01) | |
| *A61B 46/10* | (2016.01) | |
| *A61B 50/00* | (2016.01) | |
| *A61M 25/09* | (2006.01) | |

(52) U.S. Cl.
   CPC ......... *A61B 50/00* (2016.02); *A61M 25/0113* (2013.01); *A61M 25/09041* (2013.01); *A61B 2034/301* (2016.02); *A61B 2050/005* (2016.02); *A61M 2025/0166* (2013.01)

(56)                References Cited

U.S. PATENT DOCUMENTS

| | | | | |
|---|---|---|---|---|
| 2009/0082722 | A1 † | 3/2009 | Munger | |
| 2012/0179167 | A1 | 7/2012 | Wenderow | |
| 2013/0172713 | A1 | 7/2013 | Kirschenman | |
| 2014/0243742 | A1 * | 8/2014 | Pacheco | A61M 25/0113<br>604/95.04 |
| 2014/0277333 | A1 * | 9/2014 | Lewis | A61B 34/30<br>623/1.11 |
| 2015/0173838 | A1 * | 6/2015 | Murphy | A61B 34/30<br>606/130 |

* cited by examiner
† cited by third party

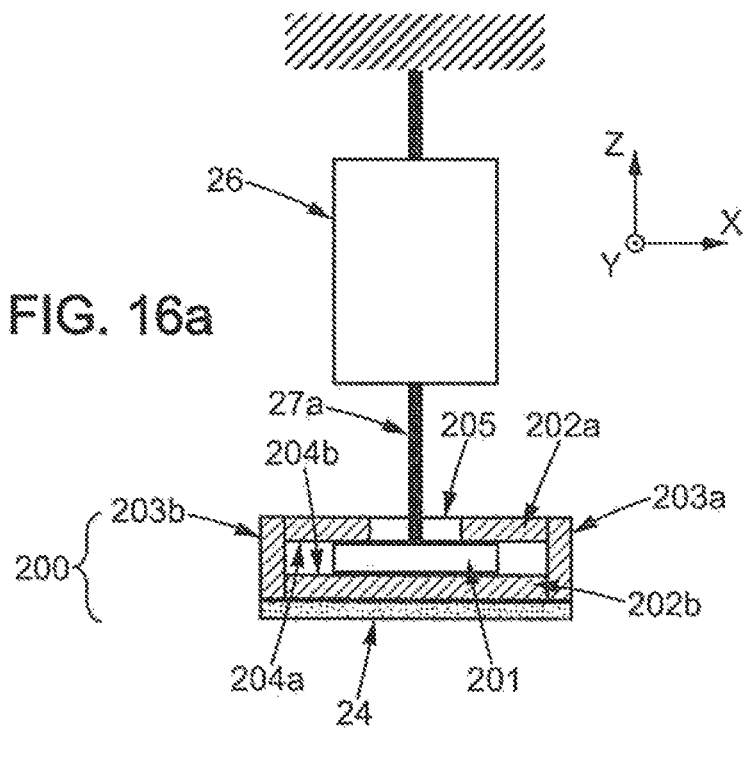
FIG. 16a
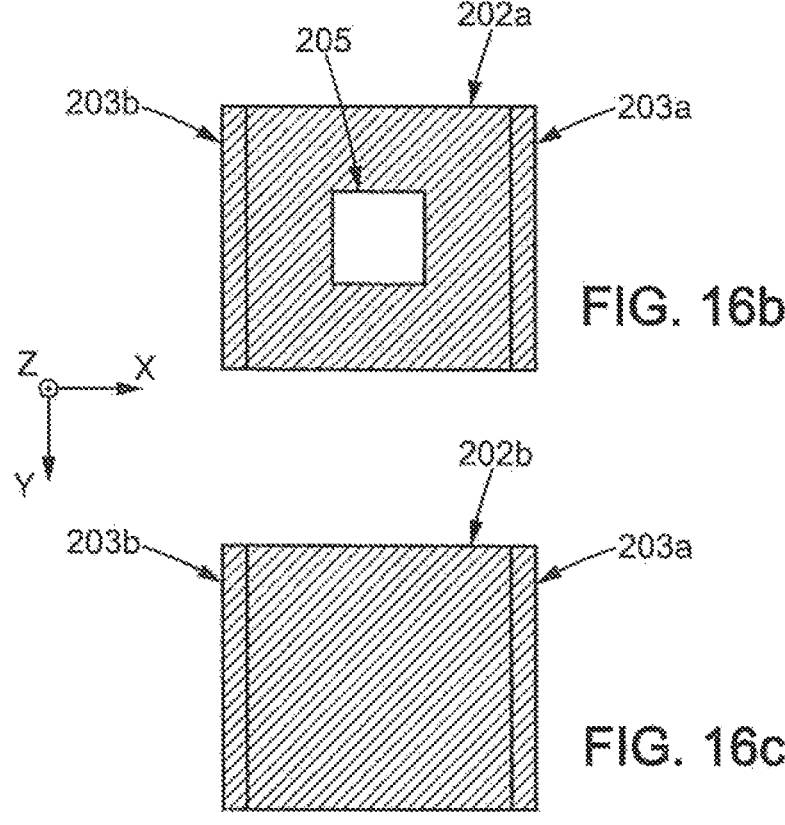
FIG. 16b
FIG. 16c

ROBOTIZED MODULE FOR GUIDING AN ELONGATE FLEXIBLE MEDICAL DEVICE

CROSS-REFERENCE TO RELATED APPLICATION

This Application is a 35 USC § 371 US National Stage filing of International Application No. PCT/FR2015/051566 filed on Jun. 12, 2015, and claims priority under the Paris Convention to French Patent Application No. 14 55330 filed on Jun. 12, 2014.

FIELD OF THE DISCLOSURE

The present invention relates to robotized modules for actuating elongated flexible medical devices.

BACKGROUND OF THE DISCLOSURE

Manually inserting a catheter or a guide into a patient is a relatively conventional surgical act. Nevertheless, since this act is monitored using X-rays, the surgeon performing the act is subjected to significant irradiation by performing such an operation on numerous patients.

In order to reduce risks for the surgeon, attempts have been made to perform such insertion robotically. Such robotization is complex, since a catheter is difficult to grip. It is immersed in a conservation liquid and it must remain sterile. Furthermore, it is desired to be able to control movements of the catheter in translation and in rotation, in alternation and/or simultaneously. The reliability of such robotized systems is a determining criterion.

Recently, U.S. Pat. No. 7,927,310 has proposed an actuation system for managing both translation and rotation of the catheter. The catheter is held on a rotary plate relative to a base for being actuated in rotation. The plate itself includes a mechanism for actuation in translation. Furthermore, use is made of remote motors, which remain permanently on the stand, and of systems for transferring movement to the catheter. Specifically, it is preferred not to have the motors embedded, for reasons of power supply, available space, and sterility.

Although that configuration gives every satisfaction, it is still desirable to simplify mechanisms of that kind, in particular for the purpose of improving reliability.

SUMMARY OF THE DISCLOSURE

To this end, the invention provides a robotized module for actuating an elongated flexible medical device, the module comprising:
a base;
a pair of actuation members each having an actuation surface, the pair of actuation members being suitable for being placed alternately in an actuation configuration wherein the actuation surfaces of the actuation members of the pair of actuation members are engaged with the elongated flexible medical device to be actuated and arranged on either side thereof, and in a free configuration wherein the actuation surface of the actuation members of the pair of actuation members is not engaged with the elongated flexible medical device;
the pair of actuation devices being movably mounted relative to the base according to a degree of freedom between a first and a second positions;
a control member suitable for controlling in a cyclically repeated manner a movement relative to the base of the actuation members of the pair of actuation members in the actuation configuration from the first to the second position, thus actuating the elongated flexible medical device relative to the base, and a movement relative to the base of the actuation members of the pair of actuation members in the free configuration from the second to the first position without actuating the elongated flexible medical device relative to the base.

Preferably, the control member is remote. Thus, there may be a single control member located in the control room, with a control member located in the operating theatre sometimes being optional, and thus capable of being omitted.

By means of these provisions, the elongated flexible medical device can be actuated, even over paths that are long and complex, by repeated simple elementary movements at the scale of the robot. The robot can thus operate regardless of the path that the catheter is to be made to follow.

In preferred embodiments of the invention, recourse may also optionally be had to any one or more of the following provisions:
the movement relative to the base of the actuation members from the first position to the second position comprises a combination of:
a translation of the actuation members relative to the base along a parallel direction to the local longitudinal direction of the elongated flexible medical device;
a translation of the actuation members relative to the base along a transverse direction to the local longitudinal direction of the elongated flexible medical device and in opposite directions;
a translation of the actuation members relative to the base along a transverse direction to the local longitudinal direction of the elongated flexible medical device and in the same direction;
a translation of the actuation members relative to the base along a transverse direction to the local longitudinal direction of the elongated flexible medical device and in the same direction;
one, two, or three terms of the combination are null;
the degree of freedom between the first and second positions is a first degree of freedom, wherein the pair of actuation members is also movably mounted relative to the base according to a second degree of freedom differing from the first degree of freedom between the first and a third positions;
the control member being suitable for controlling in a cyclically repeated manner a movement relative to the base (132) of the actuation members in the actuation configuration from the first to the third position, thus actuating the elongated flexible medical device relative to the base, and a movement relative to the base of the actuation members in the free configuration from the third to the first position without actuating the elongated flexible medical device relative to the base;
the movement relative to the base of the actuation members from the first position to the second position and the movement relative to the base of the actuation members from the first to the third position comprise two distinct combinations from:
a translation of the actuation members relative to the base along a parallel direction to the local longitudinal direction of the elongated flexible medical device;
a translation of the actuation members relative to the base along a transverse direction to the local longitudinal direction of the elongated flexible medical device and in opposite directions;

a translation of the actuation members relative to the base along a transverse direction to the local longitudinal direction of the elongated flexible medical device and in the same direction;

a translation of the actuation members relative to the base along a transverse direction to the local longitudinal direction of the elongated flexible medical device and in the same direction;

the translation of the actuation members relative to the base along a transverse direction to the local longitudinal direction of the elongated flexible medical device and in opposite directions is suitable for enabling rolling of the elongated flexible medical device on the actuation surfaces about the local longitudinal direction of the elongated flexible medical device;

the pair of actuation members is suitable for being placed from the free configuration thereof to the actuation configuration thereof by a relative movement of the actuation members relative to the base;

the first and second positions define a first degree of freedom, wherein the pair of actuation members is also movably mounted relative to the base according to a third degree of freedom from the free configuration thereof to the actuation configuration thereof;

the base is a first base, the pair of actuation members is a first pair of actuation members, the robotized module further comprising:

a second base;

a second pair of actuation members each having an actuation surface, the second pair of actuation members being suitable for being placed alternately in an actuation configuration wherein the actuation surfaces of the actuation members of the second pair of actuation members are engaged with the elongated flexible medical device to be actuated and arranged on either side thereof, and in a free configuration wherein the actuation surface of the actuation members of the second pair of actuation members is not engaged with the elongated flexible medical device;

the second pair of actuation members being movably mounted relative to the second base according to a degree of freedom between a first and a second positions;

the control member being further suitable for controlling in a cyclically repeated manner a movement relative to the base of the actuation members of the second pair of actuation members in the actuation configuration from the first to the second position, thus actuating the elongated flexible medical device relative to the second base, and a movement relative to the second base of the actuation members of the second pair of actuation members in the free configuration from the second to the first position without actuating the elongated flexible medical device relative to the second base;

the first base and the second base are rigidly connected or common;

the control member is suitable for controlling the movements of the actuation members of the first pair and of the second pair in a synchronized manner;

the control member is suitable for placing the actuation members of the first pair and of the second pair simultaneously in the actuation configuration;

the control member is suitable for placing the actuation members of the first pair and of the second pair simultaneously in the free configuration;

the control member is suitable for placing simultaneously the actuation members of the first pair and of the second pair in one case in the actuation configuration and in the other in the free configuration;

the second pair of actuation members presents certain of the above-described characteristics.

In another aspect, the invention relates to an arteriography robot having a container, an elongated flexible medical device that is contained at least in part in the container, and a robotized actuation module fastened to the container and adapted to actuate the elongated flexible medical device outside the container.

Furthermore, U.S. Pat. No. 7,927,310 has proposed an actuation system for managing both translation and rotation of the catheter. The catheter is held on a rotary plate relative to a base for being actuated in rotation. The plate itself includes a mechanism for actuation in translation. Furthermore, use is made of remote motors that remain permanently on the stand and of systems for transferring movement to the catheter. Specifically, it is preferred not to have the motors embedded, for reasons of power supply, available space, and sterility.

That configuration thus proposes a first operating mode in which the catheter and the catheter guide can advance in translation.

That configuration thus also proposes a second operating mode in which the catheter and the catheter guide can turn about themselves in the same direction, it being possible for the direction of rotation that is selected to be clockwise or counterclockwise.

However, in certain passages of the blood circulation system in the human body, such as for example at a fork in veins or arteries, or indeed for example at a lesion, it can be difficult to pass the catheter and a fortiori the catheter guide beforehand, there being a risk of coming into abutment against a wall of a blood vessel, or of catching and damaging a wall of a blood vessel, or indeed of taking the wrong blood vessel at a fork.

In order to mitigate that difficulty, an embodiment of the invention proposes adding a third operating mode in which slow translation of the catheter guide is associated with rapid alternating rotation in order to enable it to pass the sensitive zone without hindrance. Such slow translation associated with rapid alternating rotation can be applied to the guide on its own, to the catheter on its own, or to both the guide and the catheter. Even if both the guide and the catheter are being actuated, it is possible to apply this third operating mode to the guide only or to the catheter only. This aspect of the invention could be claimed separately.

To this end, the invention provides a robotized method of actuating a catheter or guide, or a catheter and guide, controlling a set of actuation members and comprising:

a first operating mode wherein the set of actuation members moves in translation the guide and/or the catheter;

a second operating mode wherein the set of actuation members rotates the guide and/or the catheter about itself;

characterized in that the method also comprises:

a third operating mode wherein the set of actuation members moves, simultaneously, in translation the guide and/or the catheter and rotates the guide and/or the catheter about itself alternately in one direction and in the other direction.

To this end, the invention also provides a robotized module for actuating a catheter or guide, or indeed a catheter and guide, comprising a set of actuation members structured and arranged in such a manner as to be capable of being controlled so as to perform the method according to any preceding claim.

To this end, the invention also provides a robotized module for actuating a catheter or guide, or indeed a catheter and guide, comprising a set of actuation members structured and arranged in such a manner as to be capable of being controlled:

in a first operating mode, in such a manner as to move in translation the guide and/or the catheter;

in a second operating mode, in such a manner as to move in translation the guide and/or the catheter; characterized in that the set of actuation members is also structured and arranged in such a manner as to be capable of being controlled:

in a third operating mode so as to cause the guide and/or the catheter simultaneously to advance in translation while also turning about itself alternately in one direction and in the other direction.

In preferred embodiments of the invention, recourse may also optionally be had to any one or more of the following provisions.

Preferably, in the third operating mode, the set of actuation members moves, simultaneously, in translation the guide and/or the catheter according to the variations of the control of a man-machine interface and automatically rotates the guide and/or the catheter about itself alternately in one direction and in the other direction. This makes it more ergonomic for the practitioner, while also providing good effectiveness in the progress of the catheter guide, while avoiding any danger for the patient of catching the wall of a blood vessel.

Preferably, in the third operating mode, the set of actuation members moves, simultaneously, in translation the guide and/or the catheter according to the variations of the control of a man-machine interface and automatically rotates the guide and/or the catheter about itself alternately in one direction and in the other direction, the alternating rotational frequency being proportional to the translation speed.

In a preferred first embodiment, in which the practitioner retains maximum freedom, there is provided a robotized method of actuating a catheter or guide, or indeed a catheter and guide, by controlling a set of actuation members and comprising:

a first operating mode wherein the set of actuation members moves in translation the guide and/or the catheter according to the variations of the control of a man-machine interface; and a second operating mode wherein the set of actuation members rotates the guide and/or the catheter about itself according to the variations of the control of a man-machine interface;

characterized in that the method also comprises:

a third operating mode wherein the set of actuation members moves, simultaneously, in translation the guide and/or the catheter and rotates the guide and/or the catheter about itself alternately in one direction and in the other direction according to the variations of the control of a man-machine interface.

In a second preferred embodiment, in which the practitioner has optimized ease-of-use, there is provided a robotized method of actuating a catheter or guide, or indeed a catheter and guide, controlling a set of actuation members and comprising:

a first operating mode wherein the set of actuation members automatically moves in translation the guide and/or the catheter;

a second operating mode wherein the set of actuation members automatically rotates the guide and/or the catheter about itself;

characterized in that the method also comprises:

a third operating mode wherein the set of actuation members moves, automatically and simultaneously, in translation the guide and/or the catheter and rotates the guide and/or the catheter about itself alternately in one direction and in the other direction.

Preferably, in the third operating mode, the set of actuation members moves, simultaneously, in translation the guide and/or the catheter and rotates the guide and/or the catheter about itself alternately in one direction and in the other direction, the ratio between the frequency of alternating rotation and the speed in translation being adjustable by the user of the method. Depending on the wishes and skill of the user, this makes it possible to adapt the ratio between the frequency of alternating rotation and the speed in translation, while optionally allowing the user to advance at the user's own pace depending on the difficulties encountered with the speed in translation that the user judges to be appropriate.

Preferably, in the third operating mode, the advance in translation of the guide and/or of the catheter is slower than in the first operating mode, whereas the alternating rotation of the guide and/or of the catheter about itself is faster than the rotation of the guide and/or the catheter about itself in the second operating mode. Thus, the increased slowness in translation coupled with the increased frequency of the alternating rotation makes passing sensitive zones more effective, even if that is at the price of expending additional energy per millimeter travelled by the guide of the catheter.

Preferably, the guide is a wire with a curved tip, the curved tip advancing along a direction parallel to the wire while turning about the axis of the wire in the third operating mode. Thus, the curved tip of the wire assists in directing the guide of the catheter in the right direction by means of this curved tip of the wire being appropriately oriented.

Preferably, the curved tip of the guide is subjected to at least two changes in direction of rotation during the time it advances over a distance corresponding to the length of the curved tip, and preferably to at least four changes in direction of rotation, and even more preferably at least ten changes in direction of rotation. Thus, the increased slowness in translation coupled with the increased frequency of the alternating rotation makes passing sensitive zones more effective, even if that is at the price of expending additional energy per millimeter travelled by the guide of the catheter.

Preferably, the guide and/or the catheter is subjected to at least two changes in direction of rotation during the time it advances over a distance corresponding to a length of 5 millimeters (mm), and preferably to at least four changes in direction of rotation, and even more preferably at least ten changes in direction of rotation. Thus, the increased slowness in translation coupled with the increased frequency of the alternating rotation makes passing sensitive zones more effective, even if that is at the price of expending additional energy per millimeter travelled by the guide of the catheter.

Preferably, in the third operating mode, the frequency of change of direction of rotation of the guide and/or of the catheter is at least 1 hertz (Hz), preferably at least 3 Hz, still more preferably at least 10 Hz.

Preferably, in the third operating mode, the speed translation of the guide and/or of the catheter is no more than 10 millimeters per second (mm/s), preferably no more than 3 mm/s, still more preferably no more than 1 mm/s.

Preferably, the third embodiment is used for passing through certain forked zones in the blood circulation system of the human body. Specifically, this third operating mode is particularly effective for passing through sensitive or difficult zones of the blood circulation system of the human body.

Preferably, the third embodiment is used for passing through certain lesion zones in the blood circulation system of the human body. Specifically, this third operating mode is particularly effective for passing through sensitive or difficult zones of the blood circulation system of the human body.

In another aspect of the invention, still for the purpose of assisting the guide and/or the catheter to pass through sensitive zones, there is provided a robotized method of actuating a catheter or guide, or indeed a catheter and guide, by controlling a set of actuation members and comprising:

a first operating mode wherein the set of actuation members moves in translation the guide and/or the catheter;

a second operating mode wherein the set of actuation members rotates the guide and/or the catheter about itself;

characterized in that the method also comprises:

a third operating mode in which the set of actuation members acts simultaneously firstly to advance the guide and/or the catheter in translation and secondly to cause the guide and/or the catheter to rotate in alternation about itself continuously in the same direction, followed by stopping such rotation.

Preferably, in the third operating mode, said rotation lasts for a shorter length of time than said stop.

Preferably, in the third operating mode, said rotation lasts for a period in the range 0.05 seconds (s) to 0.2 s, preferably about 0.1 s, said stop lasts for a period in the range 0.3 s to 1 s, preferably about 0.5 s, and said speed in translation lies in the range 1 mm/s to 5 mm/s, and is preferably about 3 mm/s.

In prior art robotized modules, whether in the medical field of catheters or in other fields, the actuators that transmit their movement to the actuation member transmit that movement via respective interfaces between the respective actuators and the base block of the actuation member.

However, in those prior art robotized modules, the interfaces are situated outside the base block of the actuation member or in a peripheral region of the base block of the actuation member.

The structure implementing those interfaces between actuators and the base block of the actuation member is then relatively simple.

An embodiment of the invention has nevertheless detected a problem of reliability in transmitting movement between actuators and the base block of the actuation member under such circumstances.

Specifically, that embodiment of the invention reveals that this problem of reliability comes from the off-center nature in the positioning of the interfaces, thereby leading to unbalanced transmission of force.

Furthermore, each actuator withstands only force in its own direction, and does not need to carry one or more other actuators in one or more other directions, as might happen in existing systems: bulk and weight are considerably reduced thereby.

That is why this embodiment of the invention proposes arranging the interfaces in such a manner that their intersection is situated in a central region of the base block of the actuation member, and preferably at the center of gravity of the base block of the actuation member, thus enabling force to be transmitted in balanced manner, leading to reliable transmission of movement between actuators and the base block of the actuation member. This aspect of the invention could be claimed separately.

This implies that the interfaces need to be located inside the base block of the actuation member, which makes it structure relatively more complex, however considerably more reliable in terms of the quality with which movement is transmitted between actuators and the base block of the actuation member.

The base block of the actuation member is secured to the actuation member and stationary relative to the actuation member.

For this purpose, in this embodiment of the invention, there is provided a movement transmission chain comprising:

a base block of a member for actuating a movable element;

three actuators controlling the block of the actuation member respectively along three mutually distinct translation directions, via three respective interfaces with the base block of the actuation member; and characterized in that the intersection of the mean surface areas of the three interfaces is located in the central region of the base block of the actuation member.

For this purpose, in this embodiment of the invention, there is provided a movement transmission chain comprising:

a base block of a member for actuating a movable element;

three actuators controlling the block of the actuation member respectively along three mutually distinct translation directions, via three respective interfaces with the base block of the actuation member; and characterized in that the three interfaces are substantially plane;

in that these three interfaces are orthogonal relative to one another;

and in that these three interfaces are interlocked in one another.

In preferred implementation of this embodiment of the invention, recourse may also optionally be had to any one or more of the following provisions.

Preferably, the three translation directions are orthogonal to one another.

Preferably, the three interfaces are substantially plane, these three interfaces being orthogonal to one another, and these three interfaces being interlocked within one another. Thus, the three interfaces can be concentrated in relatively simple and genuinely effective manner in the central region of the base block of the actuation member.

Preferably, the three interfaces are presser plates transmitting respective thrusts of the three actuators.

These plates of plane shape enable thrusts from the actuators to be transmitted in effective manner for an overall size that is relatively small.

Preferably, the first plate has two mutually orthogonal openings having the second plate and the third play passing through tem respectively, the second plate as an opening having the third plate passing through it, the opening in the second plate being orthogonal to the two openings in the first plate, while the third plate has neither the first plate nor the second plate passing therethrough. This way of interlocking the plates in one another is structurally relatively simple, while remaining effective.

Preferably, each of the openings leaves the plate passing therethrough with clearance to move, this clearance corresponding to the stroke of the actuator of the plate passing through said opening, this clearance being greater than the thickness of the plate passing through said opening. Specifically, if one of the actuators moves, the base block of the actuation member must move only in the direction corresponding to the actuator that has moved, and not in either of the two directions corresponding to the actuators that have remained stationary. For this purpose, the presence of these clearances enables the transmissions of forces coming from each of the various actuators to be independent of one another.

Preferably, each plate is movable in translation in a direction parallel to the line constituted by the intersection of the other two plates. Thus, the transmission of forces that are orthogonal in pairs between the actuators is easily maintained.

Preferably, each plate is connected to its actuator by two bars that are symmetrical relative to the first axis of said actuator, and preferably by four bars that are symmetrical relative to the trust axis of said actuator. Thus, the transmission of force coming from the actuator is well distributed over the corresponding plate.

Preferably, the base block of the actuation member is secured in stationary manner to each of the interfaces, such that the movement of any one of the interfaces leads automatically to the same movement of the base block of the actuation member. Thus, the transmission of force between the interfaces and the base block of the actuation member is more direct.

Preferably, the base block of the actuation member is a cube having the three interfaces situated inside it. Thus, the overall volume of the base block of the actuation member is relatively small, while the interfaces are nevertheless completely included inside the base block of the actuation member. Overall compactness is consequently improved.

Preferably, the base block of the actuation member is a cube resulting from assembling together eight smaller cubes that are assembled around the interfaces. These eight small cubes represent the minimum number of sub portions of the cube constituting the base block of the actuation member, in order to be able to assemble the cube around the set of three mutually interlocked interfaces.

Preferably, each plate is held between four smaller cubes on one side and four smaller cubes on the other side. The base block of the actuation member is thus completely symmetrical and balanced.

Preferably, the central region is the center of gravity of the base block of the actuation member. The transmission of forces between actuators and the base block of the actuation member is thus well-balanced because of the then well-centered nature of the interfaces relative to the base block of the actuation member.

Preferably, the movement transmission chain includes a movable element actuated by the actuation member.

Preferably, the materials used are low-friction, or even very low-friction, materials so as to allow the interfaces that are interlocked in one another to slide easily.

In a preferred, but nonexclusive, application, the movable element is a catheter or a catheter guide, and the actuation member is a member for clamping onto a catheter or a catheter guide.

In a family of embodiments, the movements of the actuators are transmitted to a corresponding pair of actuation members by an intermediate part. The actuator controls a pair of actuation members. The intermediate part transmits the movement of the actuator to the pair of actuation members, so as to translate in opposite directions the two actuation members of the pair of actuation members, while keeping the distance between the two actuation members of the pair of actuation members substantially constant, so as to rotate an elongated flexible medical device about itself when said device is arranged between the two actuation members of the pair of actuation members. The presence of this intermediate part provides greater accuracy, in so far as a movement of large amplitude of the actuator gives rise to a movement of limited amplitude of the actuation members. This aspect of the invention could be claimed separately.

Preferably, the intermediate part is a rocker converting a translation of the actuator along a first direction into two translations in opposite directions of the two respective actuation members along a second orthogonal direction to the first direction. This change in direction makes it easier to achieve the reduction in the amplitude of the movement that is transmitted.

In a first embodiment, the rocker comprises a plate that is connected to the actuator and that has two inclined oblong holes of opposing inclination wherein at least two lugs respectively connected to the actuation members slide, the inclination of the oblong holes being closer to the first direction than the second direction. This first embodiment presents the advantage of structural simplicity.

In a second embodiment, the rocker comprises a plate that is connected to the actuator and that has two inclined oblong holes of opposing inclination wherein at least two rollers respectively connected to the actuation members slide, the inclination of the oblong holes being closer to the first direction than the second direction. This second embodiment presents the advantage of less wear and longer lifetime, by using rollers instead of lugs.

In a third embodiment, the rocker comprises a plate that is connected to the actuator and that has two inclined oblique rails of opposing inclination wherein at least two slides respectively connected to the actuation members slide, the inclination of the rails being closer to the first direction than the second direction. This third embodiment presents the advantage of being more robust because of the greater area of contact between the rail and the slide.

In a first variant of the third embodiment, the two rails are in the same plane parallel to the plane formed by the first direction and by the second direction. Overall size is smaller.

In a second variant of the third embodiment, the two rails are in two distinct planes perpendicular to the plane formed by the first direction and by the second direction. Robustness is further improved since the weight of the slide on the rail acts on the entire surface of the rail and is not cantilevered out.

In a fourth embodiment, the rocker is pivoting about an axis and comprises a plate that is connected to the actuator and that has inclined oblong holes of the same inclination wherein at least three lugs or three roller respectively connected to the actuator and to the actuation members slide, the inclination of the oblong holes being closer to the first direction than the second direction, two of the oblong holes being arranged symmetrically relative to the pivoting axis and receiving the lugs or the rollers respectively connected to the two actuation members, the third oblong hole being arranged further from the pivoting axis than the two oblong holes connected to the actuation members and receiving the lug or the roller connected to the actuator.

In a fifth embodiment, the rocker comprises a plate that is connected to the actuator and that has two connecting rod and L-shaped crankshaft systems, the two L-shaped crankshafts being oriented in opposite directions, the small part of the L of the crankshafts being substantially along a first direction, the large part of the L of the crankshafts being substantially along the second direction.

In a sixth embodiment, the rocker comprises a plate that is connected on one side to the actuator and that is connected on the other side to a first end of a connecting rod the second end whereof is connected to a first end of a first rod sliding at the center thereof in a first oblong hole situated at a first end of a bar pivoting at the center thereof and the second end whereof has a second oblong hole wherein the center of a second rod slides, the oblong holes being parallel to the bar, the second ends of the two rods being respectively connected to the actuation members.

In a seventh embodiment, the rocker comprises a plate that is connected to the actuator and that has a first rack along the first direction, two second racks that are respectively connected to the actuation members and that are along the second direction and the toothed parts whereof face one another, two gear systems situated between the first rack and the respective two second racks, each of the gear systems comprising a large gear engaging with the first rack and a small gear engaging with one of the second racks. This fourth embodiment presents the advantage of structural simplicity. This seventh embodiment presents the advantage of reduced size.

In another aspect of the invention, provision is made so that the transmission of force from an actuator to the base block of the actuation member does not lead to disturbing movement in the direction of that actuator for the other actuator(s). This aspect may be claimed separately. This aspect could also be claimed in combination with any other aspect of the invention as described in this text as a whole.

Preferably, there is provided a robotized module for actuating an elongated flexible medical device, characterized in that it includes a movement transmission chain comprising:

a base block for an actuation member for actuating an elongated flexible medical device;

two actuators controlling the block of the actuation member respectively along two mutually distinct translation directions, via two respective interfaces with the base block of the actuation member; and in that each of the two interfaces allows the base block to move freely relative to its actuator in the direction associated with the other interface.

Preferably, there is also provided a robotized module for actuating an elongated flexible medical device, characterized in that it includes a movement transmission chain comprising:

a base block for an actuation member for actuating an elongated flexible medical device;

three actuators controlling the block of the actuation member respectively along three mutually distinct translation directions, via three respective interfaces with the base block of the actuation member; and in that each of the three interfaces allows the base block to move freely relative to its actuator in the two directions associated respectively with the other two interfaces.

Each actuator withstands force only in its own direction, and does not need to carry one or more other actuators in one or more other directions, as might happen in existing systems: bulk and weight are considerably reduced thereby.

The base block of the actuation member is secured to the actuation member and stationary relative to the actuation member.

For example, when the interface of the actuator for the direction X transmits a force in the direction X, the base block moves in the direction X, freely relative to the actuators in the directions Y and Z, and thus without hindering or disturbing those actuators in the directions Y and Z.

For example, when the interface of the actuator for the direction Y transmits a force in the direction Y, the base block moves in the direction Y, freely relative to the actuators in the directions X and Z, and thus without hindering or disturbing those actuators in the directions X and Z.

For example, when the interface of the actuator for the direction Z transmits a force in the direction Z, the base block moves in the direction Z, freely relative to the actuators in the directions Y and X, and thus without hindering or disturbing those actuators in the directions Y and X.

Preferably, the two or three translation directions are orthogonal to one another.

Preferably, at least one, preferably at least two, and more preferably all three, of the two or three interfaces is/are located inside the base block. This makes it possible to improve the centering of force transmission from the actuator(s) to the base block, and also to improve the accuracy and the reliability of the robotized module.

Preferably, the base block is in the form of a cube.

Preferably the material(s) of the interfaces is/are of sufficiently low friction for said free movement to be completely fluid.

This aspect could equally well be claimed separately and independently of the elongated flexible medical device, i.e. for any other type of movable element.

There is thus provided a robotized module for actuating a movable element, characterized in that it comprises a movement transmission chain comprising:

a base block of a member for actuating a movable element;

two actuators controlling the block of the actuation member respectively along two mutually distinct translation directions, via two respective interfaces with the base block of the actuation member; and in that each of the two interfaces allows the base block to move freely relative to its actuator in the direction associated with the other interface.

There is also provided a robotized module for actuating a movable element, characterized in that it comprises a movement transmission chain comprising:

a base block of a member for actuating a movable element;

three actuators controlling the block of the actuation member respectively along three mutually distinct translation directions, via three respective interfaces with the base block of the actuation member; and in that each of the three interfaces allows the base block to move freely relative to its actuator in the two directions associated respectively with the other two interfaces.

The base block of the actuation member is secured to the actuation member and is stationary relative to the actuation member.

Preferably, the two or three translation directions are orthogonal to one another.

Preferably, at least one, preferably at least two, and more preferably all three, of the two or three interfaces is/are located inside the base block.

Preferably, the base block is in the form of a cube.

Preferably the material(s) of the interfaces is/are of sufficiently low friction for said free movement to be completely fluid.

BRIEF DESCRIPTION OF THE DRAWINGS

Other characteristics and advantages of the invention appear from the following description of an embodiment

US 12,667,433 B2

Figure 1A:
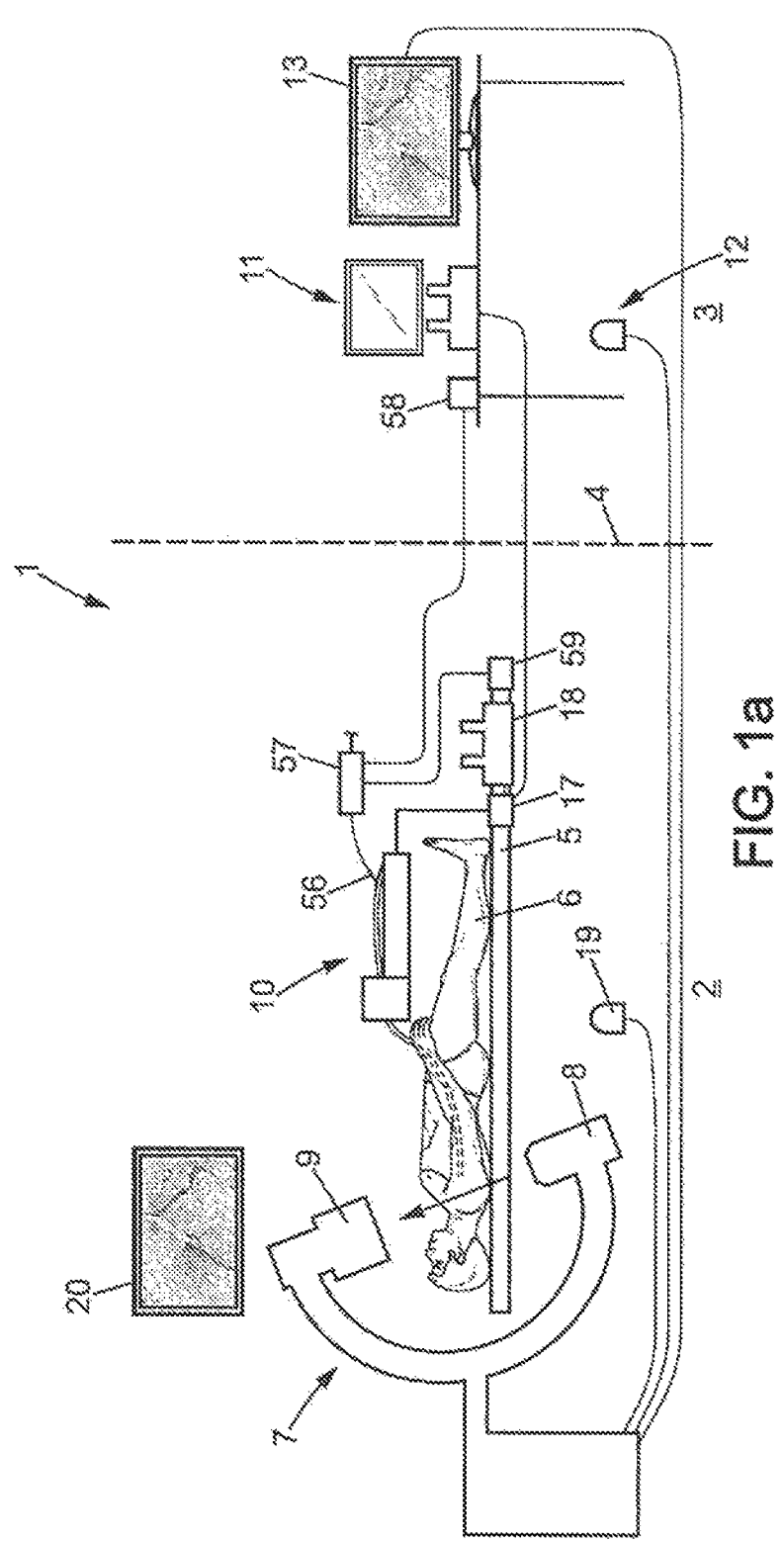

13 thereof given by way of non-limiting example and with reference to the accompanying drawings.

Figure 1B:
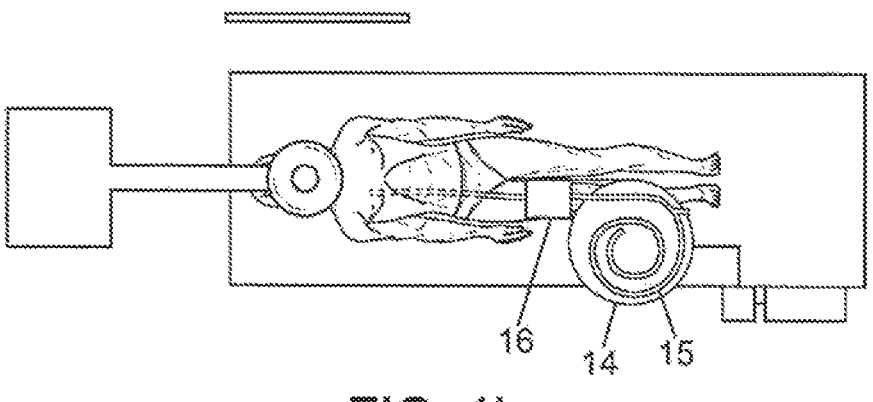
Figure 2:
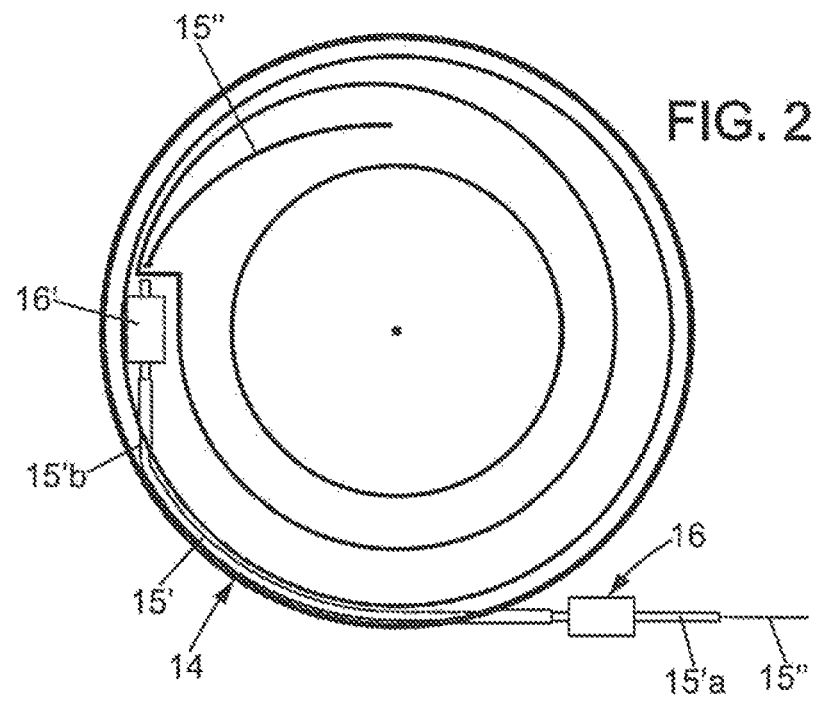
Figure 3A:
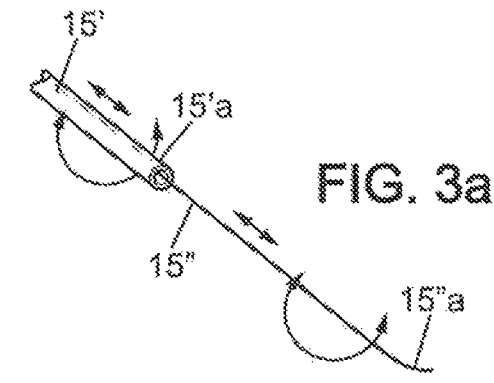
Figure 3B:
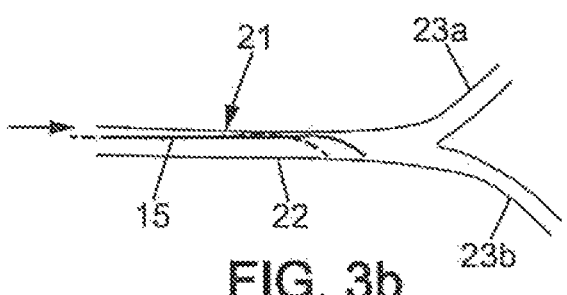
Figure 3C:
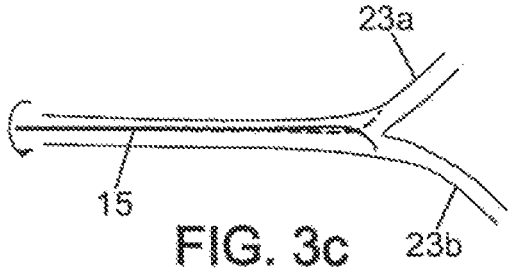
Figures 4, 5:
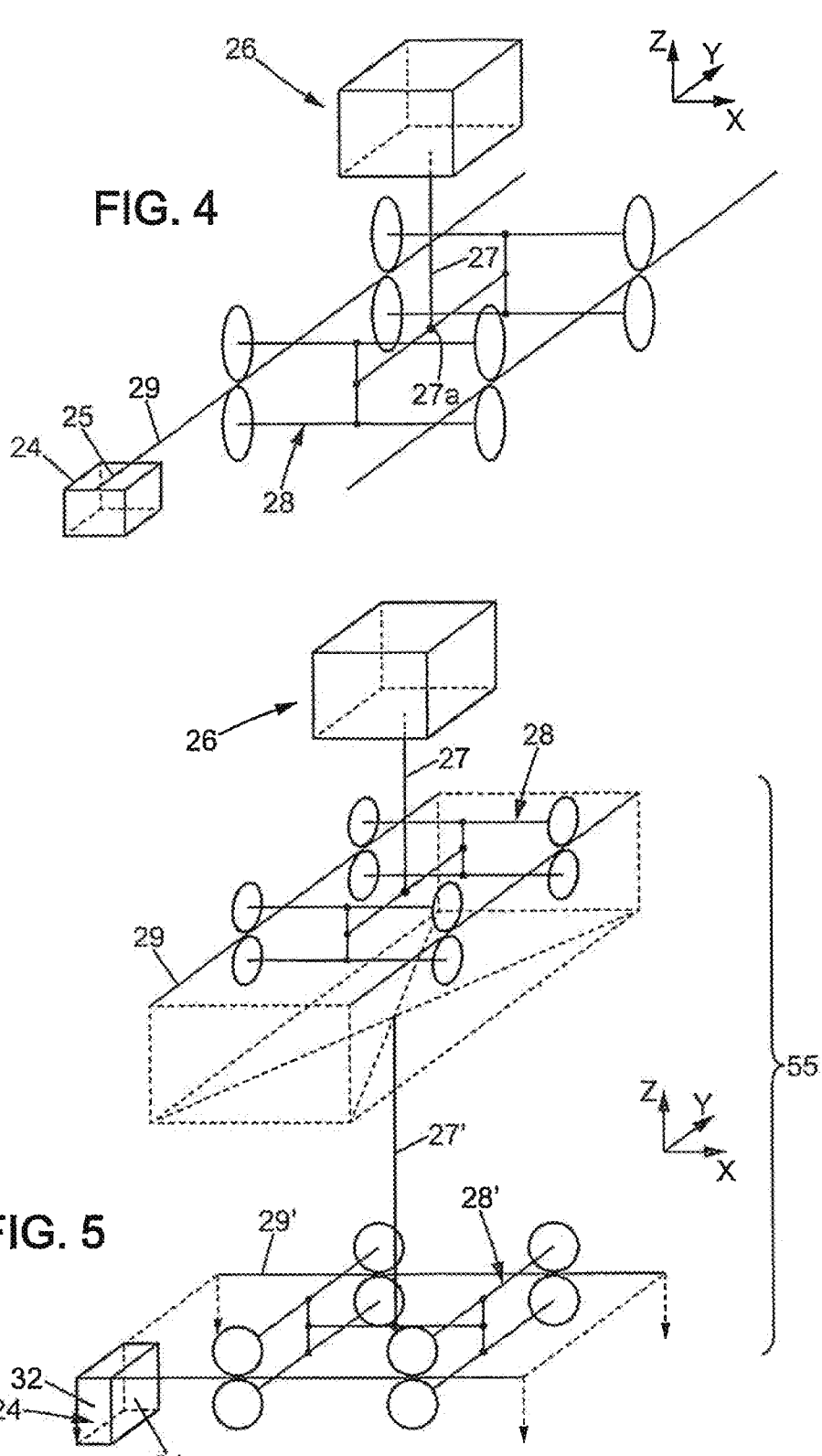
Figure 6:
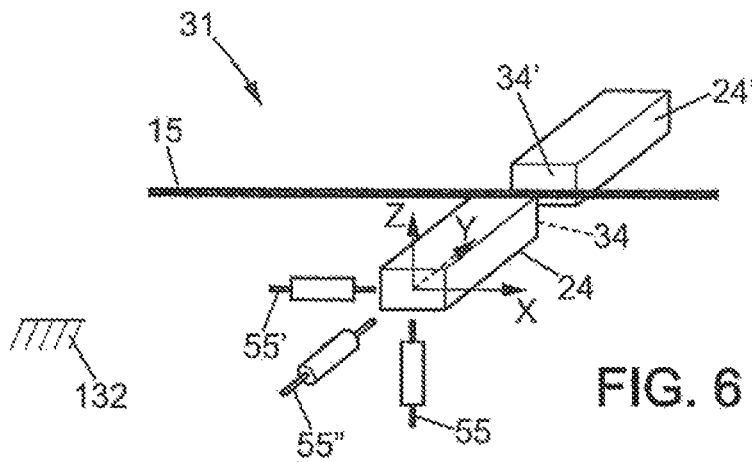
Figure 10:
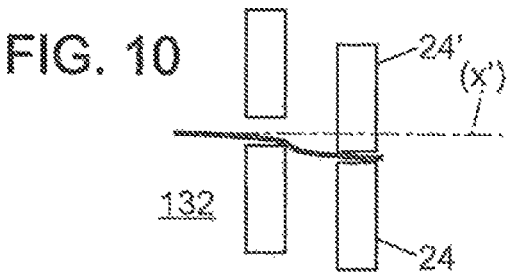
Figures 11, 12, 13:
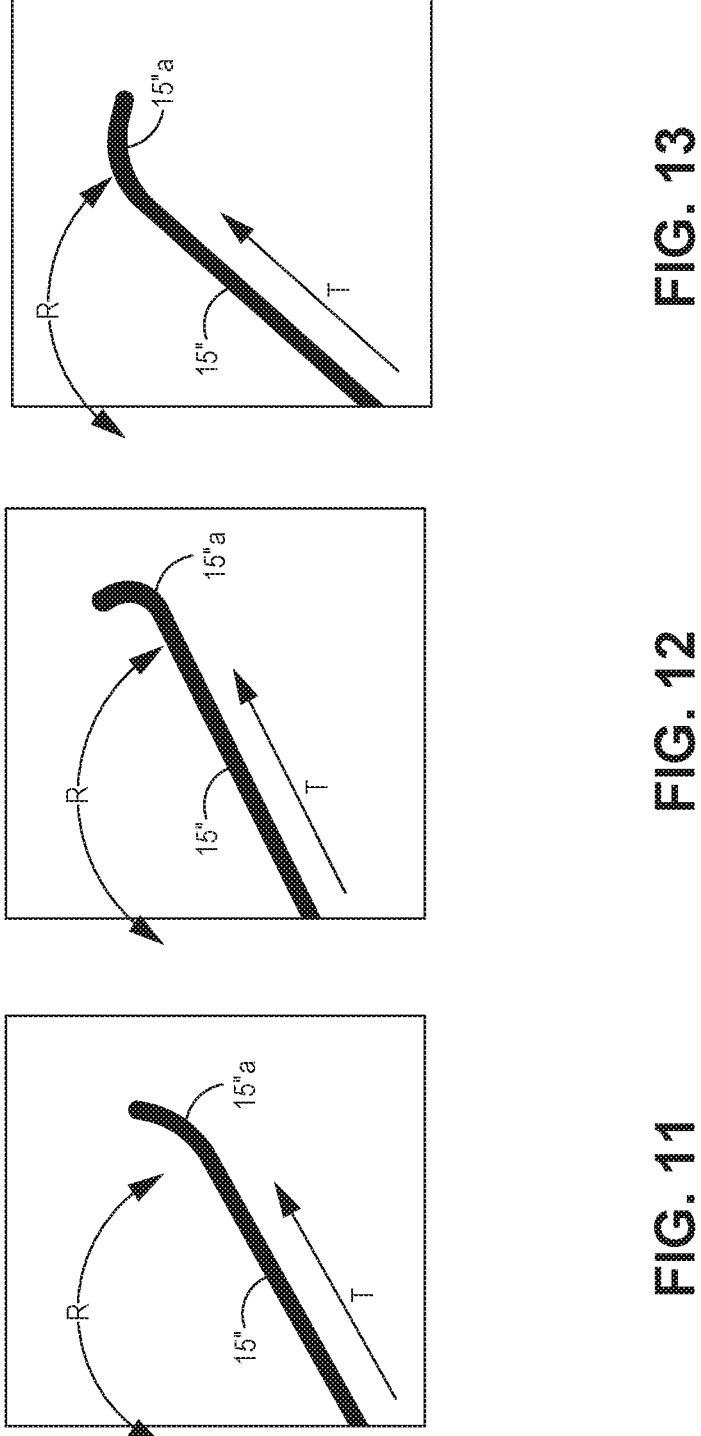
Figure 14A:
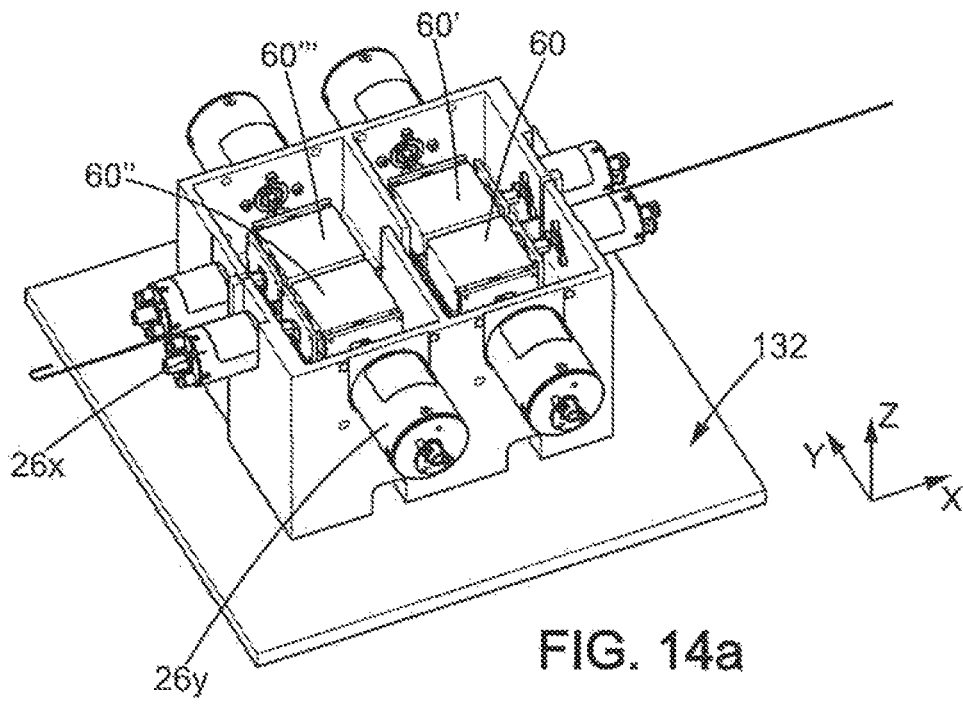
Figure 14B:
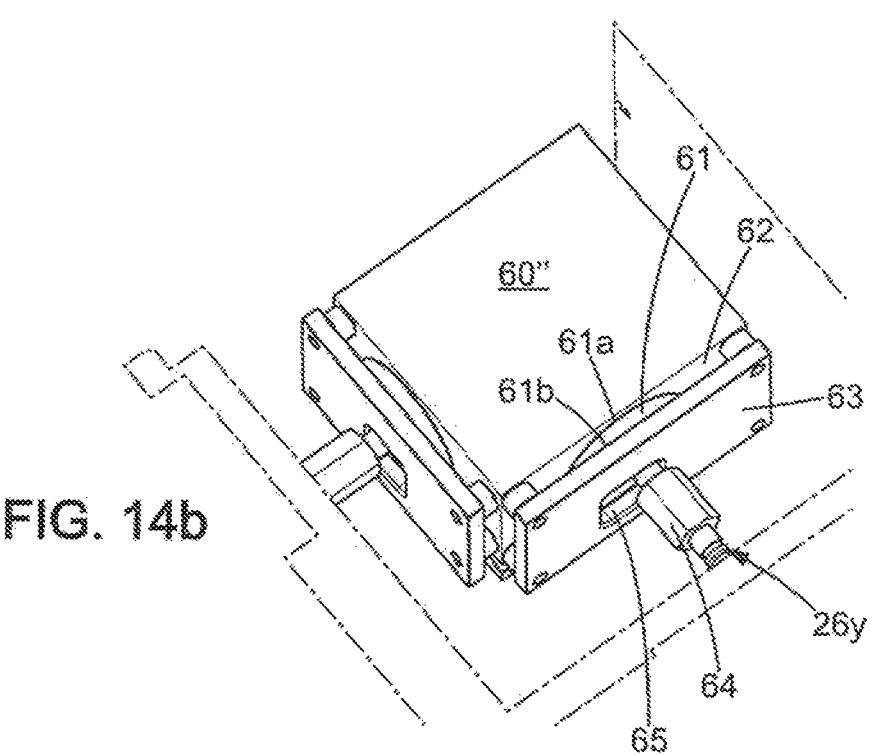
Figure 15:
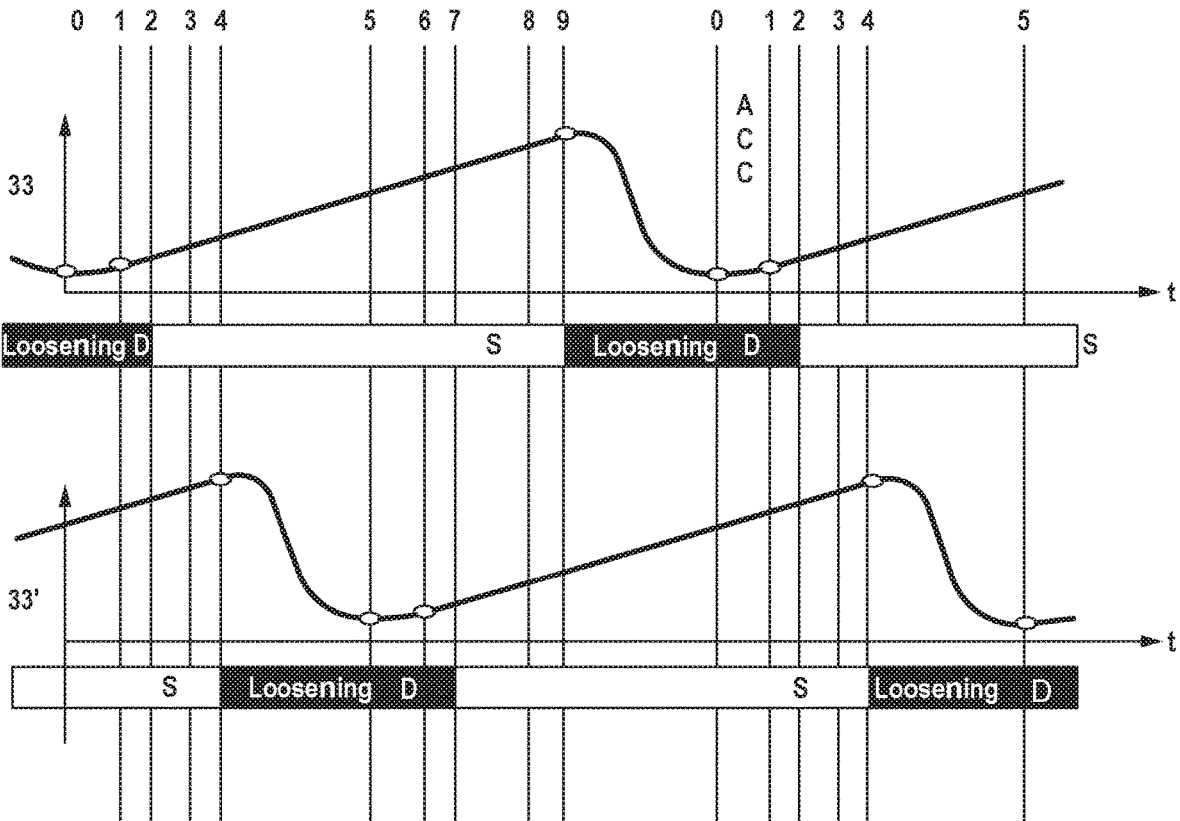
Figure 17:
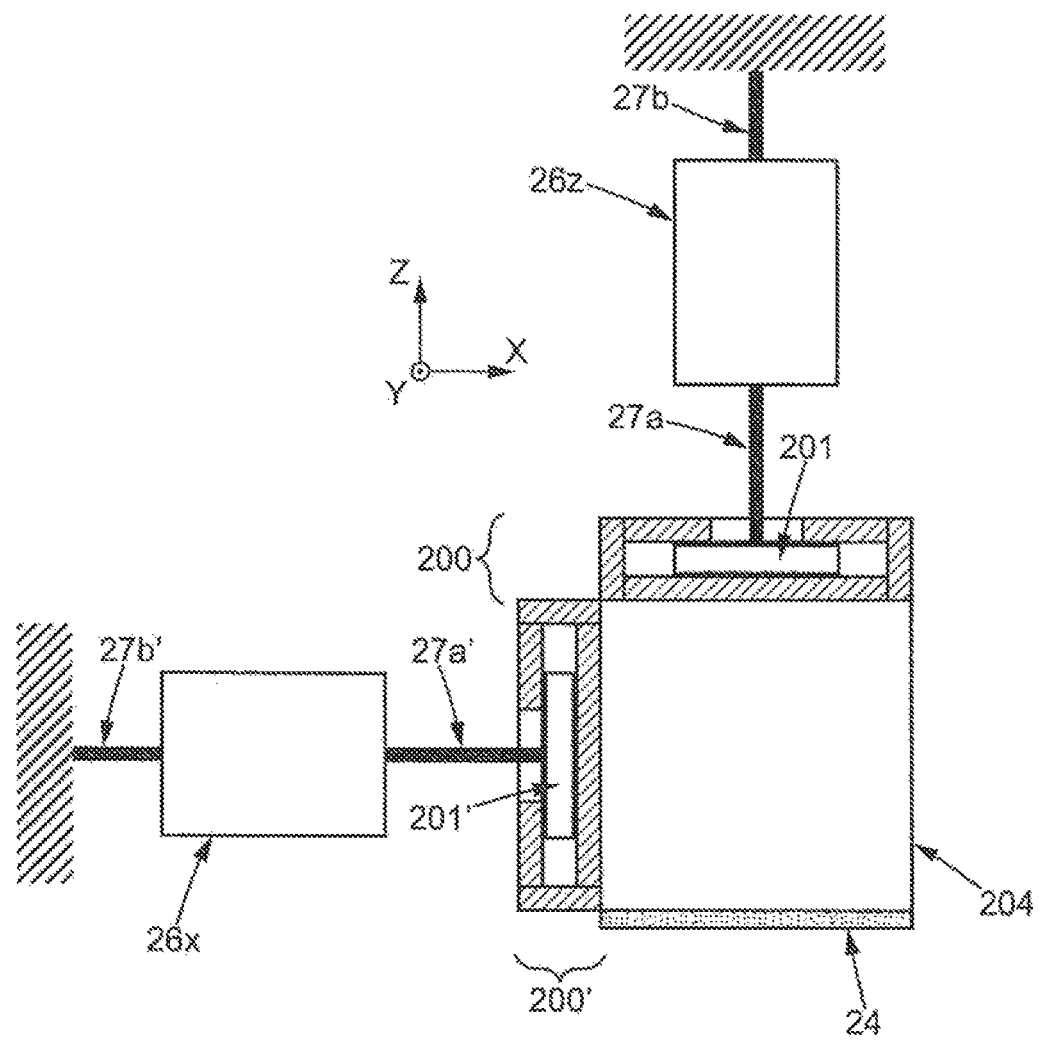
Figure 19:
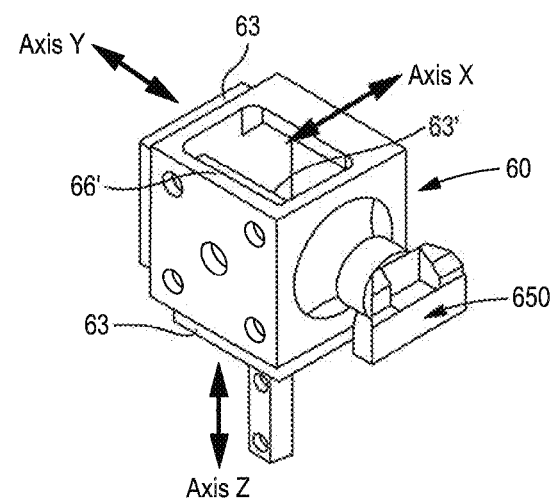
Figure 20:
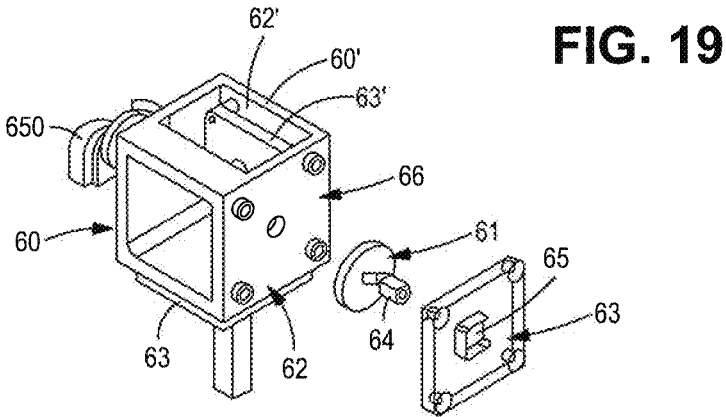
Figure 21:
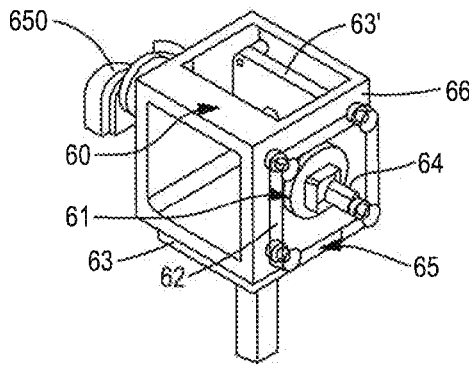
Figure 22:
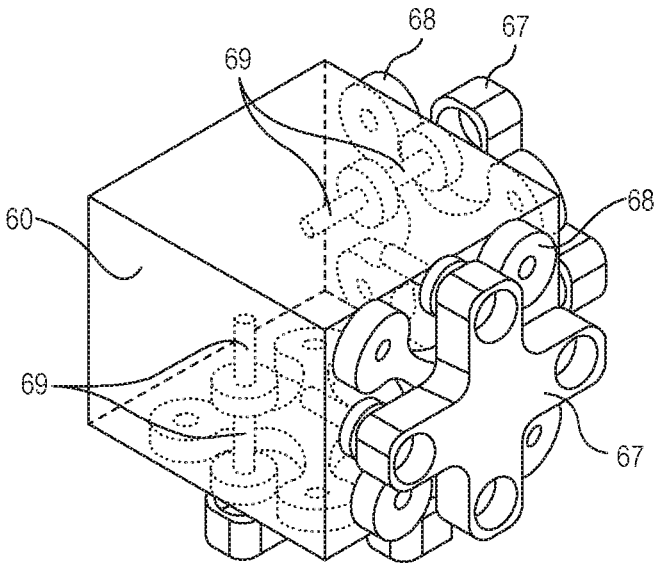
Figure 23:
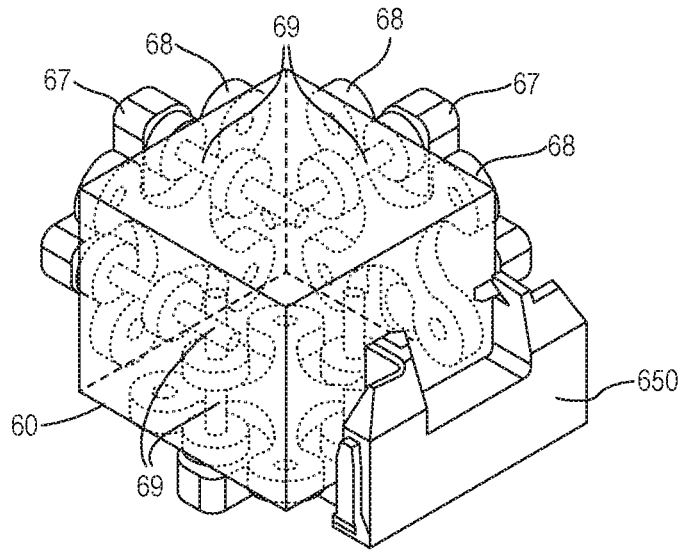
Figure 24:
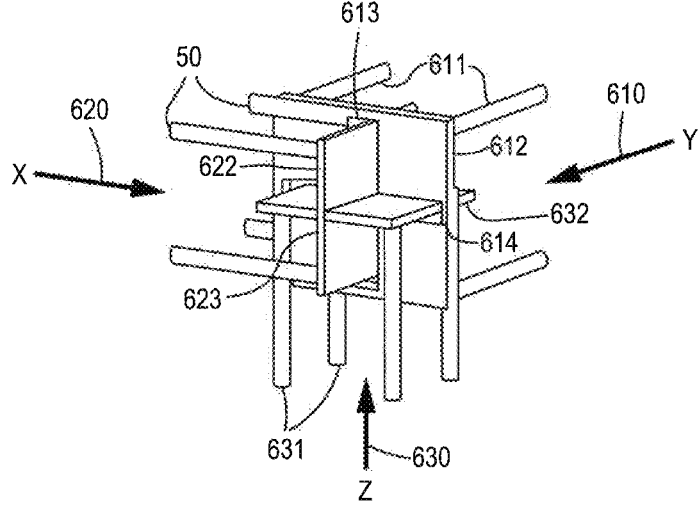
Figure 25:
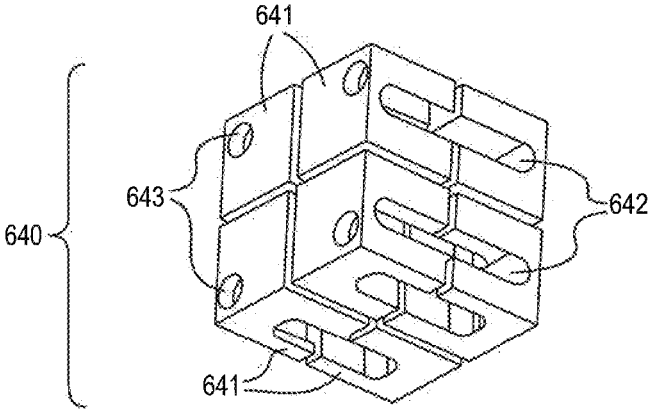
Figure 26:
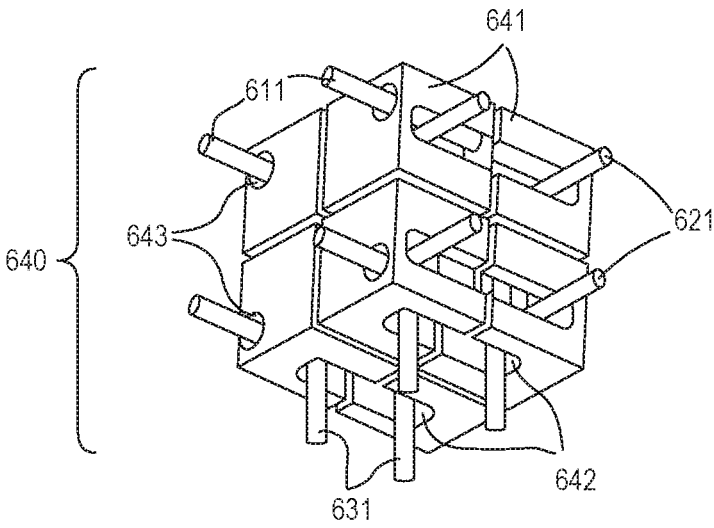
Figure 27:
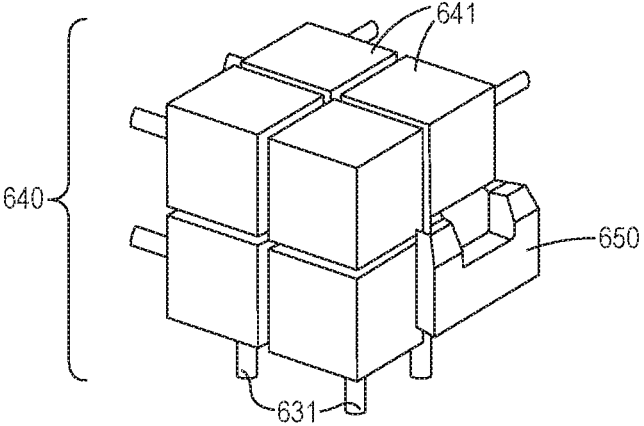

In the drawings:

FIG. 1a is a diagrammatic side view of a robotic arteriography installation;

FIG. 1b is a plan view of a portion of FIG. 1a;

FIG. 2 is a diagrammatic plan view of a robot used in the installation of FIGS. 1a and 1b;

FIGS. 3a-3c are diagrams showing modes of moving members to be actuated;

FIGS. 4 and 5 are simplified kinematic diagrams of actuating an actuation member;

FIG. 6 is a diagrammatic perspective view of a portion of an actuator module in its free configuration;

FIGS. 7a to 7e are simplified diagrams showing a cycle of actuating the catheter in translation in an embodiment;

FIG. 8a to 8e are simplified diagrams showing a cycle of actuating the catheter in rotation in an embodiment;

FIGS. 9a to 9f are simplified diagrams showing a cycle of actuating the catheter in translation in an embodiment;

FIG. 10 is a simplified diagram illustrating a crankshaft mode;

FIGS. 11-13 are other diagrams illustrating modes of moving members that are to be actuated;

FIG. 14a is a perspective view of an embodiment of an actuator system;

FIG. 14b is a detail view of FIG. 14a;

FIG. 15 is a kinematic diagram of an example of actuation in translation in an embodiment;

FIG. 16a is a plane view in the X-Z plane of an example actuator;

FIGS. 16b and 16c are two sections in two distinct planes crossing the X-Z plane of the FIG. 16a actuator example;

FIG. 17 is a plane view of a two-dimensional actuator system;

FIGS. 18a to 18m are simplified diagrams showing a portion of an actuation cycle in "crankshaft" mode of the elongated flexible medical device in an embodiment;

FIG. 19 is a perspective view of another embodiment of a cube transmitting the movements of the three actuators to the actuation member;

FIG. 20 is another perspective view of another embodiment of a cube transmitting the movements of the three actuators to the actuation member;

FIG. 21 is yet another perspective view of another embodiment of a cube transmitting the movements of the three actuators to the actuation member. This figure is similar to the preceding figure, but in this figure the assembly is shown assembled and not in an exploded view;

FIG. 22 is a perspective view of yet another embodiment of a cube transmitting the movements of the three actuators to the actuation member;

FIG. 23 is another perspective view of yet another embodiment of a cube for transmitting the movements of the three actuators to the actuation member;

FIG. 24 is a perspective view of an embodiment of the intersection and the interlocking of the interfaces between firstly actuators and secondly the base block of the actuation member;

FIG. 25 is a perspective view of an embodiment of the actuation member base block;

FIG. 26 is a perspective view of an embodiment of assembly between firstly the interfaces and secondly the actuation member base block;

FIG. 27 is another perspective view of an embodiment of assembly between firstly the interfaces and secondly the actuation member base block; and

FIGS. 28 to 35 show an intermediate part transmitting movement from an actuator to the pair of actuation members controlled by the actuator.

In the various figures, the same references are used to designate elements that are identical or similar.

DETAILED DESCRIPTION OF THE DISCLOSURE

FIG. 1a is a diagram showing an arteriography installation 1. The arteriography installation 1 is subdivided into two distinct locations, an operating theater 2, and a control room 3. The control room 3 may be close to the operating theater 2, being separated therefrom merely by a wall 4 that is opaque to X-rays, or it may be remote therefrom. The equipment in the operating theater 2 and the control room 3 is interconnected in functional manner, wirelessly, or by a network, . . . .

The operating theater 2 has an operating table 5 receiving a patient 6. The operating theater 2 may also have a medical imager 7, in particular an X-ray imager, comprising a source 8 and a detector 9 arranged on either side of the patient, and possibly movable relative to the patient.

The arteriography installation 1 includes a robot 10 located in the operating theater 2.

The arteriography installation 1 has a control station 11 arranged in the control room 3. The control station 11 is adapted to control the robot 10 remotely. The arteriography installation 1 may also include, located in the control room 3, one or more remote controls 12 for the imager 7, communicating with the imager 7 in order to control it remotely. The arteriography installation 1 may also include, located in the control room 3, a screen 13 communicating with the imager 7 and serving to display in real time in the control room 3 the images acquired by the imager 7.

The robot 10 may include a container 14 adapted to contain an elongated flexible medical device 15 for inserting in the body of a patient. By way of example, the elongated flexible medical device 15 may be a device for inserting in a canal in a patient, and for moving along that canal, in particular an artery or a vein of a patient, via a Desilet catheter introducer providing an access opening into the patient. The elongated flexible medical device may in particular be a catheter. In a variant, the elongated flexible medical device may be a catheter guide. A guide is generally of transverse diameter smaller than that of the catheter, which is generally hollow in a portion close to the patient, or indeed over its entire length, such that the guide can move inside the catheter, in particular inside the patient's body. The guide may also include a curved end, as described in greater detail below.

The robot 10 may have an actuation module 16 for actuating the elongated flexible medical device 15. The actuation module 16 is controllable from the control station 11 in order to actuate the elongated flexible medical device relative to the patient with at least one degree of freedom, as described in detail below. The actuation module may include a communication unit 17 providing interfacing with the control station 11. Where necessary, the robot 10 may include a local control unit 18 for controlling the robot from within the operating theater 2, if necessary.

It should also be observed that all of the controls and returns that are available in the control room 3 may also be available in the operating theater 2 in order to operate locally, e.g. a control 19 for the imager and a screen 20 for viewing the images acquired by the imager 7.

The hollow elongated flexible medical device 15 may be coupled to a coupling 56 enabling a contrast medium to be injected to facilitate imaging the inside of the elongated flexible medical device. The arteriography installation may include a contrast medium injector 57 coupled to the coupling 56 and controllable by a control 58 located within the control room 3. A control 59 for controlling the contrast medium injector may also be present locally in the operating theater 2.

As can be seen in FIG. 2, in purely illustrative manner, there is shown in greater detail the container 14 receiving a catheter 15'. The container 14 serves to hold the catheter 15' in a medium suitable for conserving it. The actuation module 16 is adapted to actuate the catheter 15'. In this example, provision is made for the container 14 also to receive a guide 15". The container 14 serves to hold the guide 15" in a medium suitable for conserving it. The actuation module 16' is adapted to actuate the guide 15". Depending on the application, the actuation module 16 and 16' may be identical or different. Where appropriate, they may be in accordance with one of the embodiments described below. In the example described, the guide 15" may be inserted in the catheter 15' at the rear end 15'b thereof, and may project from the front end 15'a of the catheter, as shown.

Below, the reference 15 is used to designate either the guide 15", or the catheter 15', or more generally an elongated flexible medical device for inserting into the body of a patient. By way of example, it may be an interventional catheter. Such an interventional catheter may be of smaller diameter than the catheter so as to be guided inside it, coaxially inside the patient, and it may be hollow so as to be guided on the guide inside the patient.

FIG. 3a shows the various degrees of freedom that can be envisaged with the present system. There can be seen the guide 15" with its front end 15"a that is slightly curved relative to the main longitudinal axis of the guide, and coming out through the front end 15'a of the catheter 15'. The catheter 15' may be subjected to two distinct movements:
    a translation along its longitudinal axis; and
    a rotation about its longitudinal axis.

These movements may be generated in one direction or the other. Where appropriate, the catheter 15' may be subjected to a combination of the two above-described single movements.

Where appropriate, the catheter 15' may be subjected to two combined movements of the two above-described single movements, using combinations that are different.

The above description concerning the catheter applies likewise to the guide.

In certain circumstances, the catheter is itself provided with a curved end, either to enable it to navigate on the same principle as a guide, or else to facilitate positioning in an anatomical zone presenting particular curvature.

FIG. 3b shows a patient's artery 21 having a main trunk 22 and two branches 23a and 23b running on from the main trunk. FIG. 3b shows the movement of an elongated flexible medical device 15 (specifically a guide 15") in translation between a set-back position shown in dashed lines, and an advanced position shown in continuous lines. In FIG. 3c, in the same artery, there can be seen a rotation of the elongated flexible medical device 15 between a first position, shown in dashed lines, where the elongated flexible medical device is ready to be subjected to a movement in translation towards the branch 23a, and a second position, shown in continuous lines, where the elongated flexible medical device is ready to be subjected to a movement in translation towards the branch 23b.

The elongated flexible medical device may be actuated using one or more of the above-described movements by the actuation members. These actuation members may be arranged in pairs.

FIGS. 11 to 13 show movements in translation and movements in rotation corresponding to the first and second modes of operation.

With reference now to FIGS. 3d to 3f, there follows a description of a third operating mode.

The catheter guide 15" and its curved end 15"a move in translation T along the guide 15", while simultaneously the catheter guide 15" and its curved end 15"a are subjected to alternating rotation R about the axis of the catheter guide 15"a.

The three FIGS. 3d, 3e, and 3f, show the curved end 15"a in different angular orientation positions during the alternating rotation R.

The speed of translation T is relatively slow, while the frequency of the alternating rotation R is relatively high. This third operating mode, of the type combining slow translation with simultaneous rapid alternating rotation, enables the catheter guide 15"a to pass easily through sensitive or difficult zones in the blood circulation of a human body. It is the character of rapid rotation over a short stroke in translation that enables the delicate zone to be passed without hindrance and without risk of catching in the wall of a blood vessel of the patient.

In an embodiment, a given actuation member can be actuated by an actuator.

With reference to FIG. 4, there follows a description of an actuation member 24 actuated along a single direction Z. The actuation member 24 includes an actuation surface 25 normal to the axis Z. The actuator 26 has an actuator rod 27 with an end 27a for acting on the actuation surface 25 in the direction Z. The actuation member 24 is freely movable along the direction Y without loss of contact with the actuation rod 27. The end 27a of the actuation rod 27 slides relative to the actuation surface 25 in the direction Y. By way of example, provision is made for the actuation rod 27 to be secured to a carriage 28 slidably mounted in the direction Y on rails 29 secured to the actuation member 24.

Under such conditions, if the actuation surface 25 of the actuation member 24 is moved in the direction Y, no movement of the carriage 28 is generated, and consequently no movement of the actuator 26 is generated. If the end 27a of the actuator is moved downwards (in FIG. 4) along the direction Z, then a movement of the actuation member 24 is generated downwardly along the direction Z. The travel range of the carriage 28 relative to the actuation member 24 in the direction Y is preferably limited so that, at each location of the travel range, the end 27a of the actuation rod remains engaged with the actuation surface 25 of the actuation member 24.

For a downward movement in FIG. 4, it suffices for the actuator 26 to lengthen relative to its stationary reference. For an upward movement, it suffices for it to shorten.

As can be seen in FIG. 5, the above-described mechanism can be duplicated to enable the actuation member 24 to move freely throughout the X-Y plane, and to enable actuation in the Z direction only. The mechanism shown in FIG. 4 thus corresponds to a first stage of a mechanism shown in FIG. 5, having a second stage that enables the actuation member to be driven in the direction Z but not in the direction X. For this purpose, recourse may be had to a carriage 28' that is movable along rails 29' along the axis X relative to the actuation member 24 and carrying a link rod 27' co-operating with an intermediate surface linked to the rails 29.

Under such conditions:

shortening the actuator 26 along the direction Z causes the actuation member 24 to move upwards along the direction Z;

lengthening the actuator 26 along the direction Z enables the actuation member 24 to move downwards along the direction Z;

moving the actuation member 24 along the direction X does not cause any other movement; and moving the actuation member 24 along the direction Y causes the carriage 28' to move along the direction Y relative to the carriage 28.

The actuation system 55 shown in FIG. 5 enables the actuation member 24 to be actuated in a single direction Z so long as the carriages 28 and 28' do not leave the associated rails.

The actuation system 55 may for example be based on electromagnetic or piezoelectric actuators, for example.

Provision may be made for a similar actuation system 55' to actuate the actuation member 24 along a single direction X. For this purpose, it suffices to turn the system shown in FIG. 5 through 90° about the axis Y, the rails 29' of the system then being secured to an actuation surface 31 of the actuation member 24 that is normal to the axis X.

Provision may be made for a similar actuation system for actuating the actuation member 24 in a single direction Y. For this purpose, is suffices to turn the system shown in FIG. 5 through 90° about the axis X, the rails 29' of the system then being secured to an actuation surface 32 of the actuation member 24 that is normal to the axis Y.

In another embodiment, the principle of two carriages is replaced by an assembly 200 (see FIG. 16) made up of an interface part 201, e.g. of cylindrical shape, sandwiched between two plates 202a and 202b, themselves held secured to each other, e.g. by two parts 203a and 203b, with the distance between the two inside surfaces 204a and 204b of the plates 202a and 202b being substantially equal to the thickness of the interface part 201. In order to pass the shaft 27 of the actuator 26, an opening 205 is formed in the plate 202a, e.g. an opening of substantially rectangular or square shape. An action of the actuator 26 along the axis Z then causes the actuation surface 25 of the actuation member 24, which is secured to the plate 202b, to move correspondingly along the axis Z. Simultaneously, the assembly 200 may be moved freely along the axes X and Y, the actuator 26 remaining stationary relative to these two axes. In order to allow this relative sliding movement between the interface part 21 and the assembly 200, the interface part 201 must be capable of sliding with as little friction as possible on the surfaces 204a and 204b. For this purpose, it is possible to use materials having a very low coefficient of friction. By way of example, but without this being limiting, the interface part 201 may be made of aluminum, and the parts 202a and 202b may be made of a plastics material containing polytetrafluoroethylene (PTFE).

In order to actuate the actuation member 24 no longer about only one axis but rather about two axes X and Z, two actuators 26x and 26z are used simultaneously (see FIG. 17), which actuators are placed along the direction Z for the actuator 26a and along the direction X for the actuator 26x. The actuation axis of the actuator 26z is connected via a rod 27a to an interface part 201. The actuation axis of the actuator 26x is connected via a rod 27a' to an interface part

201'. The shafts 27b and 27b' of the actuators are stationary relative to the base of the system. The interface part 201 is held by the assembly 200. The interface part 201' is held by the assembly 200'. A plate 204 secures the sets 200 and 200' together. The actuation member 24 is fastened on the plate 204, on the face opposite from the contact face between the assembly 200 and the plate 204.

Under such circumstances, a movement of the actuator 26z along its working axis Z causes a corresponding movement of the actuation surface along the same axis Z. Simultaneously, this causes the assembly 200' to slide relative to the interface part 201', this interface part 201' remaining stationary. Correspondingly, a movement of the actuator 26x along its axis X causes a corresponding movement of the actuation member 24 along the axis X, with the interface part 201 remaining stationary. Finally, simultaneous movement of the actuators 26z and 26x causes combined movement of the actuation member along the directions X and Z.

The above-described principle of movement along two axes can be extrapolated to the three dimensions of three-dimensional space by replacing the plate 204 with a cube 204' and by placing three actuators 26x, 26y, and 26z that are held by three assemblies, these three assemblies being fastened on three adjacent faces of a cube 204, and the actuation member 24 is placed on any one of the other three faces. With the three actuators secured to the base of the system by respective shafts, any movement of their respective shafts 27 along each associated direction is transmitted to the actuation surface 24, which reproduces these movements, whether they are successive or simultaneous. Thus, the actuation member can occupy any (X, Y, Z) position defined by the three windows in three-dimensional space and can follow any trajectory, its surface nevertheless retaining an orientation that is constant. Its movement range is defined simultaneously by the maximum strokes of the actuators 26x, 26y, and 26z, by the dimensions of the openings, and also by the dimensions of the interface part. Whatever the position of the elongated flexible medical device, it is thus always possible to remove it in an emergency from the robotized module.

A practical embodiment is described below with reference to FIGS. 14a and 14b.

An actuation system is thus described for actuating an actuation finger along three independent directions in three-dimensional space.

In FIG. 6, there can be seen an actuation module 131 in a first embodiment. This actuation module 131 is adapted to actuate an elongated flexible medical device 15 extending in a longitudinal direction X. It should be observed that the longitudinal direction X at the actuation module 131 is not necessarily the same as the direction X of the elongated flexible medical device 15 at its end, but a movement in translation and/or in rotation of the elongated flexible medical device 15 along/about the longitudinal direction X in the actuation module 131 leads to a translation and/or a rotation of the elongated flexible medical device 15 respectively along/around its longitudinal direction at its end.

The actuation module 131 has a base 132 and at least one actuation member 24 movably mounted relative to the base 132. By way of example, the actuation member 24 is movably mounted relative to the base 132 as explained above with reference to FIG. 5.

In the example shown, the actuation module 131 further comprises a second actuation member 24'. The actuation member 24, also referred to below as the first actuation member, and the second actuation member 24' together form a pair of actuation members 33. A pair of actuation members 33 comprises two actuation members that co-operate together to generate a movement of the elongated flexible medical device 15 relative to the base 132. In the example described, the second actuation member 24' is movably mounted relative to the base 132. By way of example, the second actuation member 24' is movably mounted relative to the base 132 as described above with reference to FIG. 5.

The first actuation member 24 and the second actuation member 24' are paired for simultaneous movement. For example, the first and second actuation members 24 and 24' may be controlled individually, independently of each other, but with respective control signals that are synchronized. In a variant, provision may be made for a common control signal to be distributed to both of the first and second actuation members 24 and 24' via a mechanical or electronic link between their control systems.

Each actuation member 24, 24' has a respective actuation surface 34, 34'. The elongated flexible medical device 15 is arranged between the actuation surfaces 34 and 34' of the actuation members 24 and 24' of the same pair. To clarify ideas, the actuation surfaces 34 and 34' are spaced apart from each other in the direction Y.

The pair of actuation members 24, 24' may be placed in a free configuration, as shown in FIG. 6, in which the actuation surfaces 34, 34' of the actuation members 24, 24' of the pair of actuation members 33 do not engage with the elongated flexible medical device 15.

The pair of actuation members 33 is placeable in a drive configuration in which the actuation surfaces 34 and 34' of the actuation members of the pair of actuation members engage with the elongated flexible medical device 15 that is to be actuated. The force applied by an actuation member to the elongated flexible medical device in this configuration may, by way of example, be of the order of a few newtons (e.g. 5 N to 30 N). By way of example, the above-described control means may be arranged to return the pair of actuation members into the free configuration, thus making it possible to provide a safety function, e.g. in the event of an electrical power supply failure.

In order to place the pair of actuation members 33 in alternation in the free and actuation configurations, it is possible to control relative movement of the two actuation members 24 and 24' towards each other. By way of example, this movement may be movement of one of the actuation members 24 relative to the base, with the other one remaining stationary. In a variant, both actuation members 24 and 24' may move towards each other relative to the base.

In this example, provision is made for movement along the direction Y.

In the embodiment described, the two actuation members 24 and 24' are movable relative to the base with one degree of freedom. This degree of freedom is different from that enabling the actuation members to be placed in alternation between the free and actuation positions. Provision is made in particular for the actuation members 24 and 24' to be movable relative to the base with one degree of freedom in their actuation configuration. Thus, movement of the actuation members with one degree of freedom in their actuation configuration generates movement of the elongated flexible medical device relative to the base 132.

An example is described in greater detail below with reference to FIGS. 7a to 7e. This example describes generating a movement in translation of the elongated flexible medical device in its longitudinal direction X.

Figures 7A, 7B, 7C:
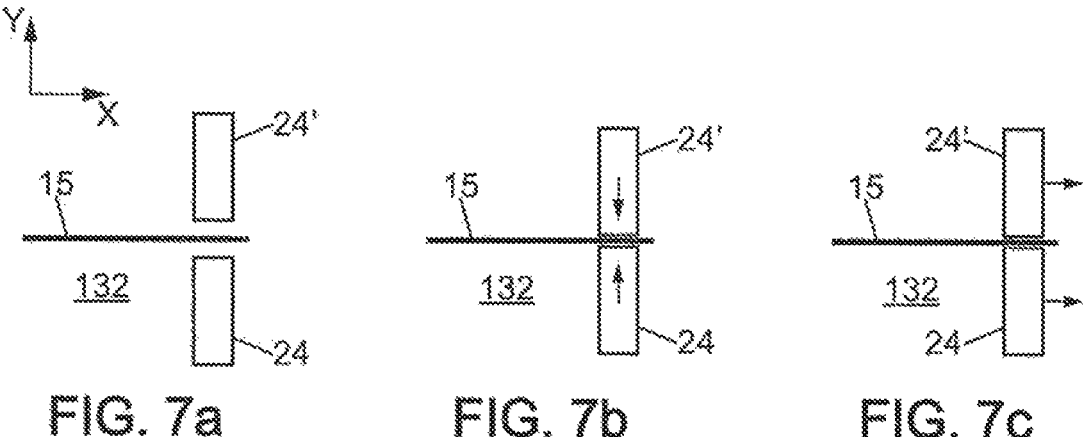

The starting position, shown in FIG. 7a, corresponds to the position in above-described FIG. 6. Initially, the free configuration shown in FIG. 7a is left in order to enter the actuation configuration (FIG. 7b). In this example, this is done by both actuation members moving in opposite directions along the direction Y. The amplitude of this movement may depend on the elongated flexible medical device 15 that is to be actuated. A guide, of diameter smaller than the diameter of the catheter, may require a movement of greater amplitude than would the catheter starting from the same starting position.

In the actuation configuration, simultaneous movement of the actuation members is generated in the same direction along the longitudinal direction X in a first direction, thereby generating an identical movement of the elongated flexible medical device 15 (FIG. 7c).

By way of example, in order to pass from the actuation configuration shown in FIG. 7c to the free configuration (FIG. 7d), the two actuation members are caused to move in opposite directions along the direction Y, in the direction opposite to the direction used for passing the actuation members from the actuation configuration to the free configuration.

Figures 7D, 7E:
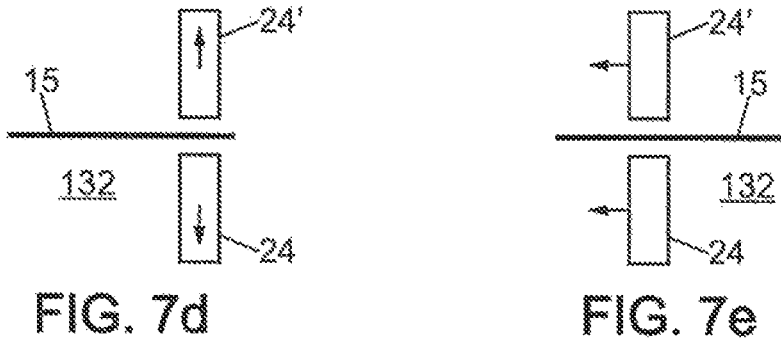

In the free configuration, optionally simultaneous movement in the same direction of the actuation members is generated in the longitudinal direction X in a second direction opposite to the first direction, thereby not generating a movement of the elongated flexible medical device 15 (FIG. 7e). This returns to the starting configuration.

The above steps may be repeated in cyclically controlled manner in order to generate translation of the elongated flexible medical device over a long stroke (e.g. of the order of several meters) in the first direction along the longitudinal direction X.

The movement of the elongated flexible medical device over a long stroke in the longitudinal direction X in the second or opposite direction may be obtained by a sequence of operations opposite to the sequence described above.

The frequency of the cycle may be adjustable and controllable. In particular, provision may be made for a low frequency while inserting the elongated flexible medical device into the patient, or indeed a plurality of low frequency levels, specifically in order to be able to navigate slowly in difficult environments. A rapid frequency may be provided, e.g. for withdrawal or indeed for emergency withdrawal. The movement amplitudes in each cycle may also be adjustable.

For translation, it is possible to envisage speeds lying in the range 0.1 mm/s to 200 mm/s.

An example is described in greater detail with reference to FIGS. 8a to 8e. This example describes generating movement in rotation of the elongated flexible medical device about its longitudinal direction X.

Figures 8A, 8B, 8C, 8D, 8E, 9A, 9B, 9C, 9D, 9E, 9F:
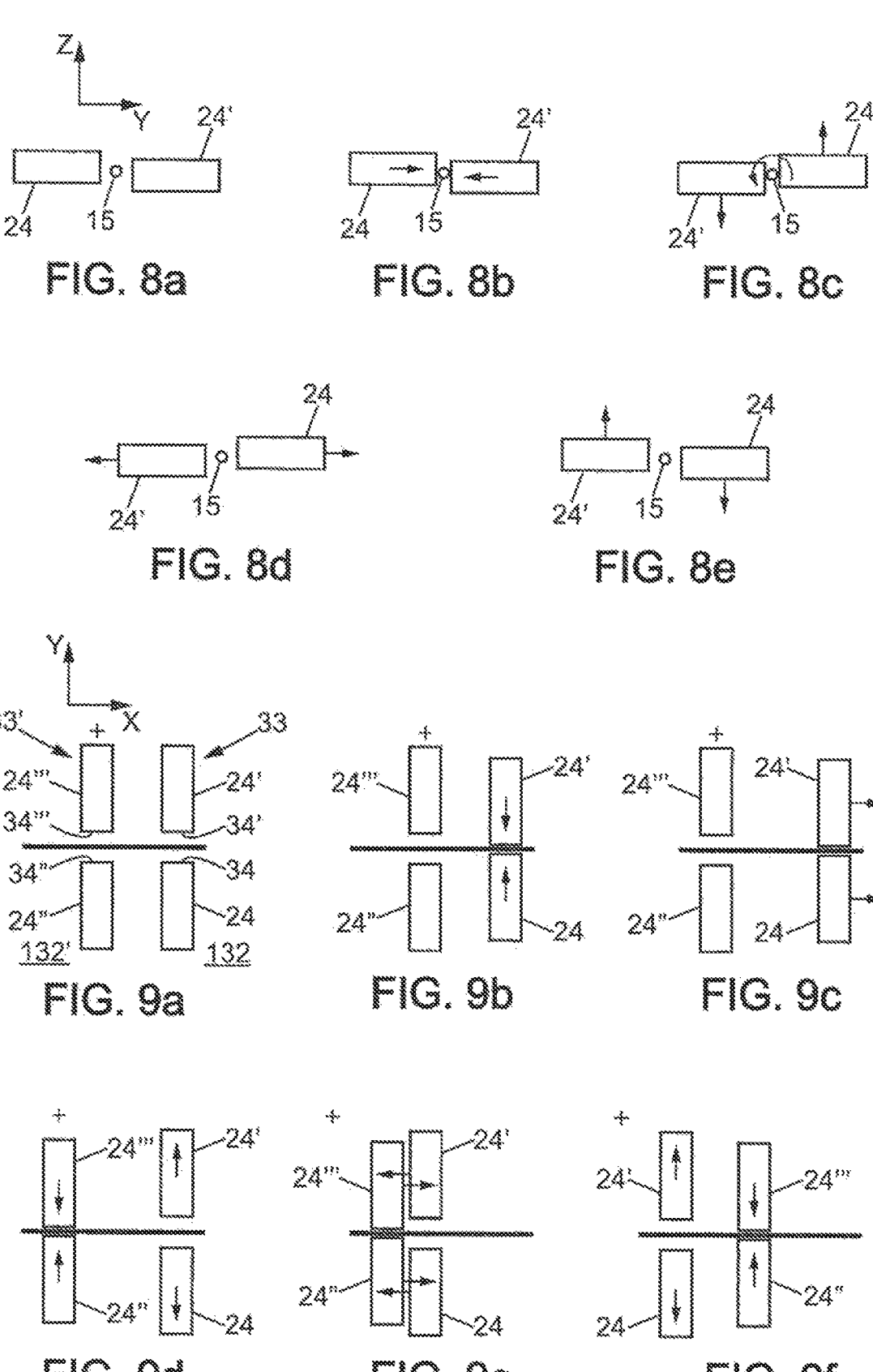

The starting position, shown in FIG. 8a, corresponds to the position in above-described FIG. 6. Initially, the system passes from the free configuration shown in FIG. 8a to the actuation configuration (FIG. 8b). In this example, this is done by moving the two actuation members in opposite directions along the direction Y. This is the same as described above with reference to FIGS. 7a and 7b.

In the actuation configuration, the actuation members are caused to move simultaneously in opposite directions along a direction Z extending transversely relative to the longitudinal direction X and different from the direction Y, thereby generating a movement in rotation of the elongated flexible medical device 15 (FIG. 8c) about the longitudinal direction X. In particular, the elongated flexible medical device rolls, preferably without slipping, on the actuation surfaces 34 and 34' of the actuation members 24 and 24'. In a variant, it would be possible to move only one of the actuation members, with the other one remaining stationary.

The system passes from the actuation configuration shown in FIG. 8c to the free configuration (FIG. 8d). By way of example, this may be done by moving the two actuation members in opposite directions along the direction Y, in the direction opposite to the direction for causing the actuation members to pass from the actuation configuration to the free configuration.

In the free configuration, optionally simultaneous movement of the actuation members is generated along the direction Z, opposite to the movement described above with reference to FIG. 8c, which does not generate movement of the elongated flexible medical device 15 (FIG. 8e). This returns to the starting configuration.

It is possible to repeat the above steps in cyclically controlled manner in order to generate rotation of the elongated flexible medical device over a long stroke (e.g. over several times 360°) about the longitudinal direction X in a first direction of rotation.

The movement of the elongated flexible medical device over a long stroke about the longitudinal direction X in the second direction of rotation opposite to the first may be undertaken by a sequence of operations opposite from the above-described sequence.

In the above description, the degree of rotation of the free end of the flexible medical device inside the patient's body may be monitored by imaging. Nevertheless, in a variant or in addition, it is also possible to seek to monitor the amplitude of the rotation applied to the flexible medical device upstream, i.e. at the actuation module. This relies on knowing the diameter of the elongated flexible medical device where it passes through the actuation members 24 and 24'. Specifically, the angle of rotation of the elongated flexible medical device for a given movement of the actuation members depends on the ratio between the diameter of the elongated flexible medical device and the stroke of the actuation members. This diameter may be predefined and stored in the control station 11. It suffices to inform the control station 11 beforehand of the type of catheter in use, where the type in question specifies its diameter. In a variant, it is also possible to detect the diameter of the elongated flexible medical device in situ. If the free configuration of each actuation member constitutes a reference position, it is possible to discover the position of the actuation member in the actuation configuration, e.g. by using a coding system on the actuator associated with each actuation member and enabling the actuation member to be moved from its free configuration to its actuation configuration.

Knowing the position of the two actuation members in the actuation configuration, and knowing the spacing between the actuation surfaces 34 and 34' in their free configuration, it is possible to determine the spacing between the two actuation surfaces in the actuation configuration, and thus the diameter of the elongated flexible medical device.

This knowledge may also be used to detect the end of a movement of withdrawing the elongated flexible medical device. Specifically, if the control station 11 detects a sudden change in the diameter detected over time while causing the elongated flexible medical device to be withdrawn, that very likely means that the elongated flexible medical device has been completely withdrawn from the patient, and even from the module. The diameter that is then detected may either be null, or else by way of example the diameter of the guide if the guide then extends between the two actuation members.

It is also possible to control the clamping of the elongated flexible medical device in the actuation configuration.

Specifically, in the actuation configuration, the current applied to the actuators is proportional to the clamping force applied to the elongated flexible medical device. Knowing this current thus makes it possible to determine the clamping that is applied to the catheter. In practice, various current setpoints may be provided in the control station 11 for the actuators, occupying a range of clamping that is acceptable and outside which there is a risk either of the elongated flexible medical device sliding out of engagement, or else of damaging the elongated flexible medical device by the actuation members applying excessive mechanical stress.

The clamping of the elongated flexible medical device may be under control for any movement that is applied to the catheter, and not only for the above-described movement in rotation.

The diameter of the elongated flexible medical device could be determined for ways of causing the catheters to move other than the presently-described cyclically repeated control signal.

Thus, independently of the presently-described cyclically repeated control signals, it appears that another invention relates to a robotized module for actuating an elongated flexible medical device comprising:

a base 132;

a pair 33 of actuation members 24, 24' each having an actuation surface 34, 34', the pair 33 of actuation members 24, 24' being suitable for being placed by at least one actuator 26 in an actuation configuration wherein the actuation surfaces 34, 34' of the actuation members 24, 24' of the pair 33 of actuation members 24, 24' are engaged with the elongated flexible medical device to be actuated and arranged on either side thereof;

the pair 33 of actuation devices 24, 24' being movably mounted relative to the base 132 according to a degree of freedom between a first and a second positions;

a control member 18, 11 suitable for responding to a representative signal relating to the actuator 26 to control (e.g. in a cyclically repeated manner) a movement relative to the base 132 of the actuation members 24, 24' of the pair 33 of actuation members 24, 24' in the actuation configuration from the first to the second position, thus actuating the elongated flexible medical device relative to the base 132.

In particular, the representative signal relating to the actuator serves to determine a spacing between the actuation surfaces 34, 34', the control member 18, 11 controlling a movement determined from the spacing relative to the base 132 of the actuation members 24, 24' of the pair 33 of actuation members 34, 34', thus actuating a rotation of controlled amplitude of the elongated flexible medical device relative to the base 132.

In particular, the representative signal relating to the actuator makes it possible to control a clamping force applied to the elongated flexible medical device over an acceptable range of clamping forces.

In both the above embodiments, a sequenced movement is described during which there is a wait until the movement of an actuation member in one direction has terminated before beginning another movement.

Nevertheless, given that the actuations of the actuation members in various degrees of freedom can be made independent by making use in independent manner of the three above-described actuation systems 55, 55', and 55", it is possible to implement simultaneous movement of an actuation member with two degrees of freedom. For example, moving the actuation members from the position of FIG. 8c to the position of FIG. 8e could include an intermediate stage between a first stage of pure moving apart and a second stage of pure return to the initial position, in which these two movements are combined. A similar intermediate stage can also be envisaged between the position of FIG. 8d and the position of FIG. 8b between the stage of pure return to the initial position and a stage of pure moving together. Continuing on these lines, it is possible no longer to have stages of pure return to the initial position, pure spacing apart, and pure moving together, providing there is no risk of generating interfering movements of the elongated flexible medical device.

Furthermore, although with reference to FIGS. 7a-7e there is described an independent movement in pure translation of the elongated flexible medical device, and with reference to FIGS. 8a-8e a pure movement of rotation, those two movements could alternatively be combined. It would suffice, in an engaged configuration, to combine the appropriate movements of the actuation members in order to generate translation and rotation simultaneously.

The above example has a single pair of actuation members.

In a variant, provision could be made for a plurality of pairs of actuation members. For example, by way of description, it would be possible to provide two pairs of actuation members. The actuation members 24" and 24''' of the second pair 33' may be similar to those of the first pair, and in particular thus may have actuation surfaces 34" and 34''' and be actuated from the remote control station 11, or indeed from the local control unit 18 in implementations similar to those of the first pair. The first pair 33 and the second pair 33' of actuation members may be offset relative to each other along the longitudinal axis X of the elongated flexible medical device. In a first example, the two pairs 33 and 33' may be arranged to be coplanar in their free configuration, i.e. they may be provided facing a base 132 that is common to both pairs. In a variant, the bases 132 and 132' of each of the pairs could be independent, and indeed not coplanar.

The actuations of the two pairs may be synchronized. For example, the actuations of the two pairs may generate simultaneous identical movements of the two pairs.

In a variant, the two pairs may be actuated in synchronized manner in order to generate movements that are offset in phase. I.e. a first pair 33 may be in an actuation configuration while another pair is in a free configuration, and vice versa. For example, there may always be at least one pair in the actuation configuration. At each given moment, that may be the first pair, the second pair, or indeed both simultaneously. Such a configuration makes it possible to improve holding of the elongated flexible medical device. In particular, when the elongated flexible medical device is moved while rubbing against an anatomic zone of the patient, it is necessary to be able to ensure that it is held sufficiently to overcome the local resistance to movement. This is made that much more difficult when the elongated flexible medical device is slippery, e.g. because it is maintained in a solution.

By way of illustration, an example is given in FIGS. 9a to 9f for a mode of actuation in translation. In these figures, a reference that is stationary over time is indicated by the "+" sign. The movement of the first pair, shown in FIGS. 9a to 9e has already is described above with reference to FIGS. 7a to 7e. FIG. 9f shows the same position as FIG. 9b, the movement being cyclical.

FIGS. 9b to 9f show the movements of the second pair 33' during a cycle. These movements are out of phase relative to the movements of the first pair, the position shown in FIG.

9d for the second pair corresponding to the position shown in FIG. 9b for the first pair, and so on.

The two pairs are spaced apart so as to avoid any collision, in particular as shown in FIG. 9e, where the second pair is subjected to movement in the forward direction of the elongated flexible medical device and where the first pair is subjected to movement in the opposite direction.

By way of illustration, FIG. 9a shows a state that may be an initial state in which both pairs are situated at a distance from the elongated flexible medical device. When the system is put into operation, the first pair is operated and then subsequently the second pair, in phase-shifted manner.

This implementation applies to movements other than movements in translation. This implementation applies to more than two pairs. Under such circumstances, where appropriate, the pairs may all be mutually phase-shifted relative to one another, or certain pairs may be in-phase with one another.

FIG. 15 describes a concrete example of synchronizing the two pairs 33 and 33'. The following cycle is described with reference to the first pair 33, it being understood that the pair 33' is in phase-opposition relative thereto.

Step 0: acceleration to reach target speed.

Step 1: once speed is reached, it is maintained at a constant level and the clamping order is given so as to achieve effective clamping at the beginning of step 2; at the same time, the second pair 33' is still at full speed, with clamping activated.

Step 2: clamping is applied and speed remains constant.

Step 3: clamping continues and speed remains constant; at this moment, the second pair 33' receives the unclamping order, which becomes effective at the beginning of step 4 after a certain delay (associated with the mechanical and electronic response time of the system as a whole); in all, it can be considered that there has been a period of simultaneous actuation by both pairs beginning at the beginning of step 2 and terminating at the beginning of step 4.

Step 3: clamping and constant speed continue.

Step 4: clamping and constant speed continue; at this stage, the second pair 33' returns to its origin position and waits stationary in its origin position; this waiting time is variable as a function of the speed setpoints for translation and rotation, and also as a function of the total cycle time.

Step 5: clamping and constant speed continue; the second pair 33' reaches the beginning of its cycle, i.e. the equivalent of step 0 for the first pair 33.

Step 6: clamping and constant speed continue; the second pair 33' terminates its acceleration and reaches the beginning of the constant speed stage (equivalent to step 1 for the first pair 33).

Step 7: clamping and constant speed continue; clamping becomes effective for the second pair 33'.

Step 8: the unclamping order is issued while maintaining constant speed; there is necessarily a certain delay before the unclamping order becomes effective, and it is therefore necessary to continue at constant speed throughout that delay.

Step 9: it is considered that unclamping is now effective, and the order is given to return to the initial position, for the following cycle, and once the return has been completed, the pair waits at the initial position until the beginning of the following cycle.

When the diameter of the elongated flexible medical device is detected by using at least two pairs of actuation members, it is possible to detect that the end of a step of withdrawing the elongated flexible medical device has been reached if two pairs of actuation movements serve to determine diameters that are different. This occurs when an upstream pairs still detects the presence of the elongated flexible medical device between its actuation members, while a downstream pair no longer detects it (detecting only a guide or else nothing). Such detection makes it possible to stop operating the downstream actuation members if there is no need for them to actuate the guide. Furthermore, and independently, such detection makes it possible, where necessary, to stop complete withdrawal of the elongated flexible medical device, thereby making it possible, where applicable, to insert the elongated flexible medical device once again into the patient without manual intervention for reengaging the elongated flexible medical device in the actuation module.

In the above-described embodiments, the actuation members are arranged symmetrically about a general midplane of the elongated flexible medical device.

Nevertheless, in a variant, the actuation members could be mounted to move relative to the base 132 in order to cause the elongated flexible medical device to shift laterally locally relative to its neutral longitudinal axis X'. The neutral longitudinal axis X' is defined as the longitudinal axis that is naturally occupied by the elongated flexible medical device without any action thereon by the actuation means 24. Such a lateral shift is possible by causing the actuation members 24 and 24', while in an engaged configuration, to move simultaneously in the same direction along a transverse direction (axis Y or axis Z, or a combination of both of these axes) relative to the engaged configuration at the neutral longitudinal axis.

Where applicable, if a plurality of actuation members are used, they may be arranged in the engaged configuration with different lateral offsets relative to the neutral longitudinal axis. It is then possible to implement actuation of the "crankshaft" type.

Figures 18A, 18B, 18C, 18D, 18E, 18F, 18G:
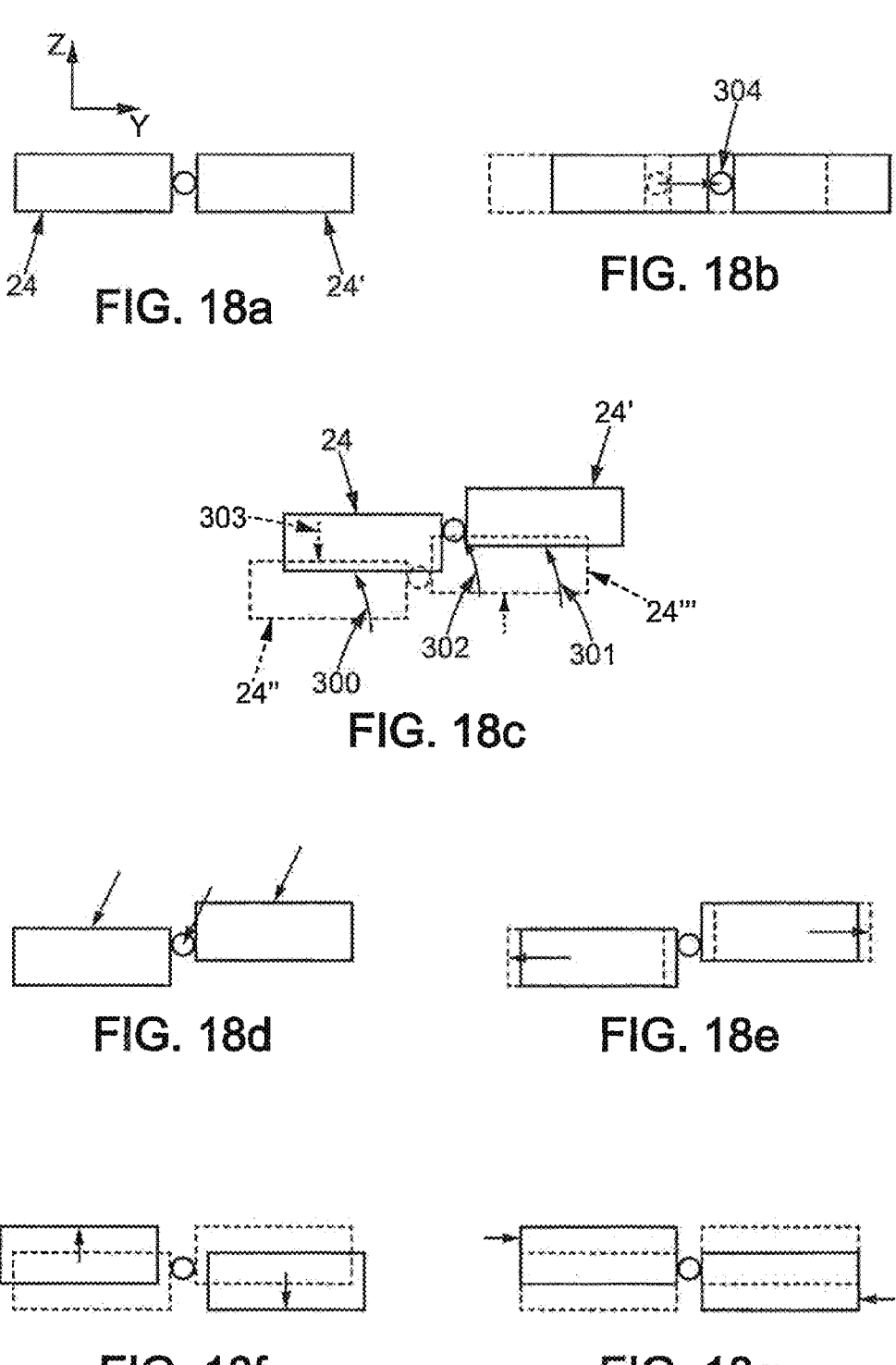
Figures 18H, 18I, 18J, 18K, 18L, 18M:
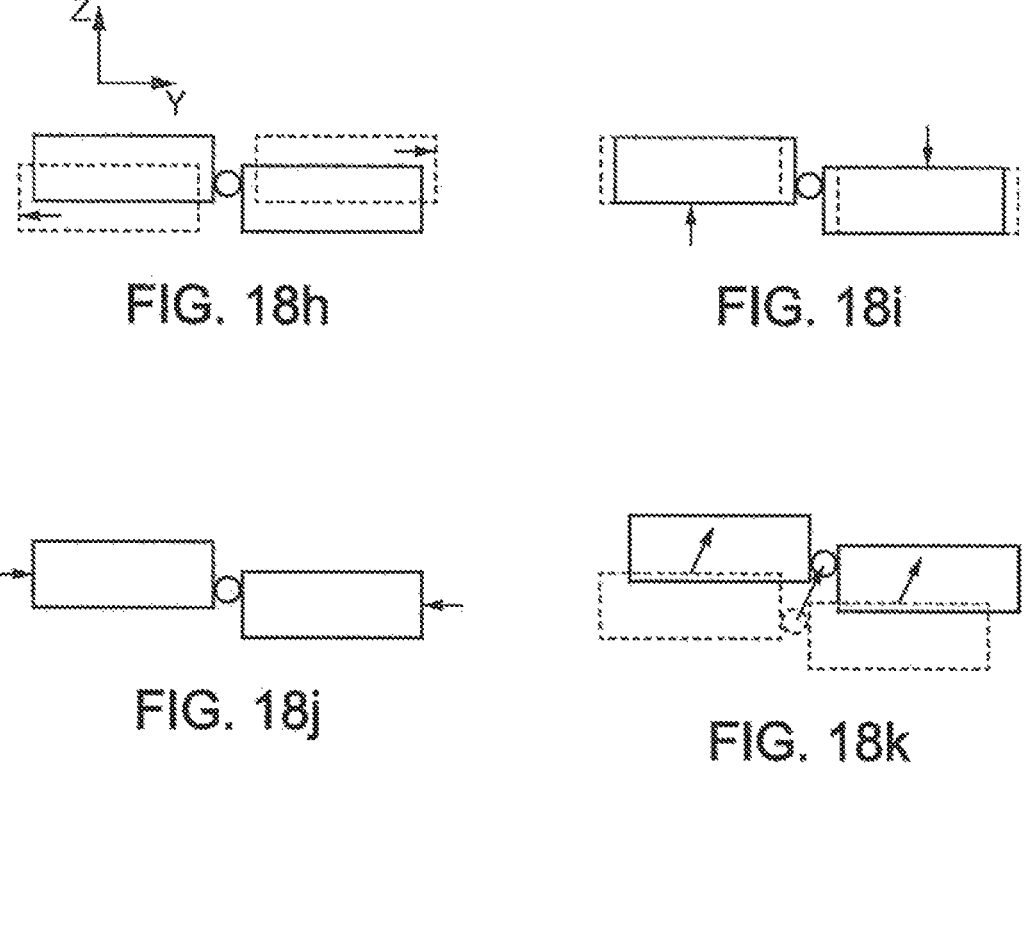

FIG. 18a is a face view corresponding to the configuration of FIG. 10, lying in the plane of the first pair of actuation members 24 and 24' shown in FIG. 10. The elongated flexible medical device 15 in this plane is drawn in continuous lines. The position of the elongated flexible medical device in the plane of the second pair of actuation members is drawn in dashed lines. The same code of continuous lines or dashed lines is applied to the second pair of actuation members is in the actuation configuration in order to continue the description (FIGS. 18a to 18m).

FIGS. 18a to 18m show how this mode is performed. As in FIG. 10, the two pairs of actuation members are shown one behind the other. The pair (24", 24''') that is situated behind is drawn in dashed lines. The elongated flexible medical device is shown twice, in the form of two sections, one section 304 in the first pair (the foreground), is drawn in continuous lines, and the other section in the second pair of actuation members (in the background) is drawn in dashed lines:

18a: initial position;
18b: first pair shifted to the right;
18c: the center of gravity of the first pair (24, 24') describes a circular arc about the axis defined by the elongated flexible medical device in FIG. 18a. Simultaneously, both pairs move in translation in the direction Z, each actuation member moving in a direction opposite to the other actuation member in the same pair. For each element of the first pair (24, 24'), it can thus be seen that path followed is the vector sum of a straight line path and a circular path. As a result, two rising curves are obtained, but nevertheless with a smaller radius of curvature for the curve 300 of the actuation member 24 than for the curve 301 of the actuation member 24'. This is associated with the fact that the path of the actuation member 24 is the sum of a circular arc identical to the path 302 of the elongated flexible medical device, directed approximately upwards, plus a straight line path directed downwards, identical to the path 303 of the actuation 24" and directed downwards;

18d: the first pair returns to the origin position, such that the elongated flexible medical device is once more guided along a straight line;
18e: unclamping the first pair, the second pair remaining clamped;
18f: movement along the direction Z of both actuation members of the first pair and in opposite directions so as to obtain a final Z position that is symmetrical to the initial position relative to the elongated flexible medical device;
18g: clamping the first pair;
18h: unclamping the second pair, while the first pair remains clamped;
18i: moving the second pair in the direction Z identically to 18f for the first pair;
18j: clamping the second pair;
18k: returning the first pair of actuators to the final position of 18c;
18l: movement similar to 18c but with a different circular arc (it should be observed that it is still be possible to use the same circular arc instead of using a succession of circular arcs making up a complete circle, as shown herein);
18m: the first pair returning to the position as in 18d; and etc.

The above-described implementation is a diagrammatic representation of a non-limiting combined implementation of movements of two actuation members in a single pair with a combination of two degrees of freedom, implementing successive movements of two actuation members of the same pair with two different degrees of freedom, and combining the implementation of two independent pairs of actuation members.

A practical embodiment of such a system is described below with reference to FIGS. 14a and 14b. This embodiment is provided solely by way of illustration of a concrete embodiment of an actuation system.

FIG. 14a comprises a stationary base 132 common to four actuation systems. Each actuation system controls the movement of a respective actuation member (not shown) that is secured to a respective cube 60, 60', 60", 60'''. The cubes 60, 60', 60", 60''' correspond respectively to the actuation members 24, 24', 24", 24''' in FIG. 9a, with substantially the same orientation.

Consequently, the operation of only one cube is described. By way of example, reference is made to the cube 60". The cube 60" is associated with three actuators 26x, 26y, and 26z (not visible but entirely similar to the actuators 26x and 26y, and situated under the base 132). The actuator 26y is used to move the cube 60" in the direction Y, while allowing the cube 60" to move in both the directions X and Z relative to the actuator 26y over a certain range of movement.

As can be seen in FIG. 14b, the actuator 26y has one end secured to a disk 61 of large diameter. This disk 61 is placed in a slot 62 provided between the cube 60" and a plate 63 secured thereto. In particular, the thickness of the slot 62 and of the disk 61 correspond, so that one surface 61a of the disk is in contact with the cube 60″ and an opposite surface 61*b* is in contact with the plate 63.

The arm 64 passes through a window 65 formed in the plate 63. The window 65 is of a shape such that the disk 61 cannot escape from the slot 62 through the window 65. The window 65 defines the range of movement allowed for the cube relative to the actuator 26*y* in the directions Y and Z.

The other actuators present similar configurations in their respective orientations.

Consequently, during extension of the actuator 26*y*, the disk 61 pushes against the cube 60″ in the direction Y, and causes it to move in that direction. When the actuator 26*y* retracts, the disk 61 pulls on the plate 63 in the direction Y and generates a movement of the cube 60″ that is secured thereto in this direction. These movements are authorized over ranges of movements as authorized by the windows in the plates associated with the actuators 26*x* and 26*z*.

When another actuator, e.g. the actuator 26*x*, generates a movement of the cube 60″ in the direction X in the same manner, that movement is possible within the limits authorized by the dimension of the window 65 in the direction X (and likewise for the plate associated with the actuator 26*z* in this example).

FIG. 19 is a perspective view of another embodiment of a cube for transmitting the movements of the three actuators to the actuation member.

The cube 60 still has the same three actuators 26*x*, 26*y*, and 26*z* acting respectively along the directions X, Y, and Z. The actions of these actuators 26*x*, 26*y*, and 26*z* are represented by respective double-headed arrows. Two of the interfaces between actuators 26*y* and 26*z* and the cube 60 are arranged on the outside faces of the cube 60, as in the above-described embodiment. One of the interfaces, the interface between the actuator 26*x* and the cube 60, operates on a similar principle but, in contrast, it is arranged inside the cube 60, thereby enabling the assembly constituted by these interfaces and the cube 60 to be more compact. This interface comprises a plate 63′ that is thus arranged inside the cube 60, facing an inside wall 66′ of the cube 60. On one of the faces of the cube 60 that does not include an actuator interface, there is secured a touch endpiece 650. This endpiece 650 may be secured in stationary manner to the actuation member 24 that it carries and that is described with reference to FIG. 6.

FIG. 20 is another perspective view of another embodiment of a cube for transmitting the movements of the three actuators to the actuation member.

In more detailed manner, for one of the outside interfaces of the actuator, specifically of the actuator 26*y*, there can be seen the disk 60 and the arm 64 forming the shoe, the arm 64 passing through the window 65 in the plate 63. The disk 61 moves in similar manner to the above-described embodiment in the slot 62. The assembly is shown in an exploded view.

The inside interface for the actuator 26*x* with its plate 63′ operates in similar manner, but the movement of its disk 61 in the plane of the plate 63′ takes place between the inside wall 66′ of the cube 60 and the plate 63′ in a slot 62′. For example, as above, the thrust of the disk 61 perpendicularly to the surface of the inside wall 66′ of the cube 60 and/or of the plate 63′ enables the cube 60 to move along the axis X, only.

FIG. 21 is yet another perspective view of another embodiment of a cube for transmitting the movements of the three actuators to the actuation member. This figure is similar to the above figure, but in this figure the assembly is shown assembled, and no longer in an exploded view.

FIG. 22 is a perspective view of yet another embodiment of a cube for transmitting the movements of the three actuators to the actuation member.

The operation of the cube 60 is similar to that of the above-described embodiment, but its structure is different. Specifically, the disk 61 is replaced by a cross 67. This cross-shape 67 for the presser shoe serves to distribute forces better over the cube 60 and to limit jamming. Collared lugs 69 extend the cross 67 at the ends of its four branches towards the inside of the cube 60. Another cross 68 having its branches arranged between the branches of the cross 67 is situated between the outside wall of the cube 60 and the cross 67. By way of example, the actuator pushes against the center of the cross 67 that in turn pushes the cube 60 via the four collared lugs 69 so as to spread the thrust force over the entire face of the cube 60.

FIG. 23 is another perspective view of yet another embodiment of a cube for transmitting the movements of the three actuators to the actuation member. The cube 60 is seen from another side. The cube 60 also carries a touch endpiece 650 likewise secured and fastened to the actuation member 24 described with reference to FIG. 6. In this embodiment, likewise, in a variant, one of the actuator interfaces may be arranged inside the cube 60, as in the preceding embodiment.

FIG. 24 is a perspective view of an embodiment of the intersection and interlocking of interfaces between actuators and the base block of the actuation member.

Three actuators 610, 620, and 630 exert forces in three mutually orthogonal directions X, Y, and Z.

The actuator 610 exerts its force in the direction Y via four bars 611 pushing against the four corners of a first presser plate 612 that constitutes the interface between the actuator 610 and the base block of the actuation member. The first plate 612 has a first opening 613 with a second plate 622 passing therethrough, which second plate constitutes the interface between the actuator 620 and the base block of the actuation member. This first opening 613 includes clearance in the direction X so as to accommodate the stroke of the actuator 620 and the associated second plate 622 in the direction X without moving the first plate 612. The first plate 612 has a second opening 614 through which there passes a third plate 632 constituting the interface between the actuator 630 and the base block of the actuation member. This second opening 614 has clearance in the direction Z so as to accommodate the stroke of the actuator 630 and of the associated third plate 632 along the direction Z without moving the first plate 612.

The actuator 620 exerts its force along the direction X via four bars 621 pushing against the four corners of a second presser plate 622, which constitutes the interface between the actuator 620 and the base block of the actuation member. The second plate 622 has a third opening 623 with a third plate 632 passing therethrough that constitutes the interface between the actuator 630 and the base block of the actuation member. This third opening 623 has clearance in the direction Z so as to accommodate the stroke of the actuator 630 and of the associated third plate 632 in the direction Z without moving the second plate 622.

The actuator 630 exerts its force in the direction Z via four bars 631 pushing against the four corners of a second presser plate 632 that constitutes the interface between the actuator 630 and the base block of the actuation member. The third plate 632 does not have any opening.

FIG. 25 is a perspective view of an embodiment of the actuation member base block.

The base block of the actuation member comprises a cube 640 that could be any of the cubes 60, 60', 60", or 60''' of FIG. 14*a*. This cube 640 comprises eight small cubes 641 assembled together at the eight vertices of the cube 640. In reality, the small cubes 641 are only portions of small cubes, occupying only three faces. Some of the faces of the small cubes 641 have circular openings 643, while other faces of the small cubes 641 have oblong openings 642. The circular openings 643, like the oblong openings 642, are for receiving the bars 611, 621, and 631 of the various plates 612, 622, and 632.

FIG. 26 is a perspective view of an embodiment showing how the interfaces are assembled with the actuation member base block.

The bars 611, 621, and 631 of the various plates 612, 622, and 632 can penetrate to a greater or lesser extent in the various openings 642 and 643, thus enabling the plates 612, 622, and 632 respectively to move the cube 640 in the directions Y, X, and Z, respectively. The plates 612, 622, and 632 push or pull the small cubes 641 together making up the cube 640.

FIG. 27 is another perspective view of an embodiment of assembling together the interfaces and the actuation member base block.

From this view point, the small cubes 641 do not have any openings, but only a touch endpiece 650. This endpiece 650 can carry in secure and stationary manner the actuation member 24 described with reference to FIG. 6.

In the following FIGS. 28 to 35, there can be seen an intermediate part for transmitting the movement of an actuator to the pair of actuation members controlled by the actuator. The intermediate part shown transmits the movement of the actuator to the pair of actuation members in such a manner as to move the two actuation members of the pair of actuation members in translation in opposite directions, while keeping substantially constant the spacing between the two actuation members of the pair of actuation members, so as to rotate an elongated flexible medical device about itself when said device is arranged between the two actuation members of the pair of actuation members. The intermediate part is a rocker generally transforming a translation of the actuator in a first direction into two translations in opposite directions of the two respective actuation members in a second direction orthogonal to the first direction. In all of these figures, double-headed arrow H represents a horizontal translation in both directions (go and return), while double-headed arrow V represents vertical translation in both direction (go and return). The horizontal and vertical directions are relative to the orientation of the figures and have no bearing on the real directions of the actuators and of the actuation member.

Figure 28:
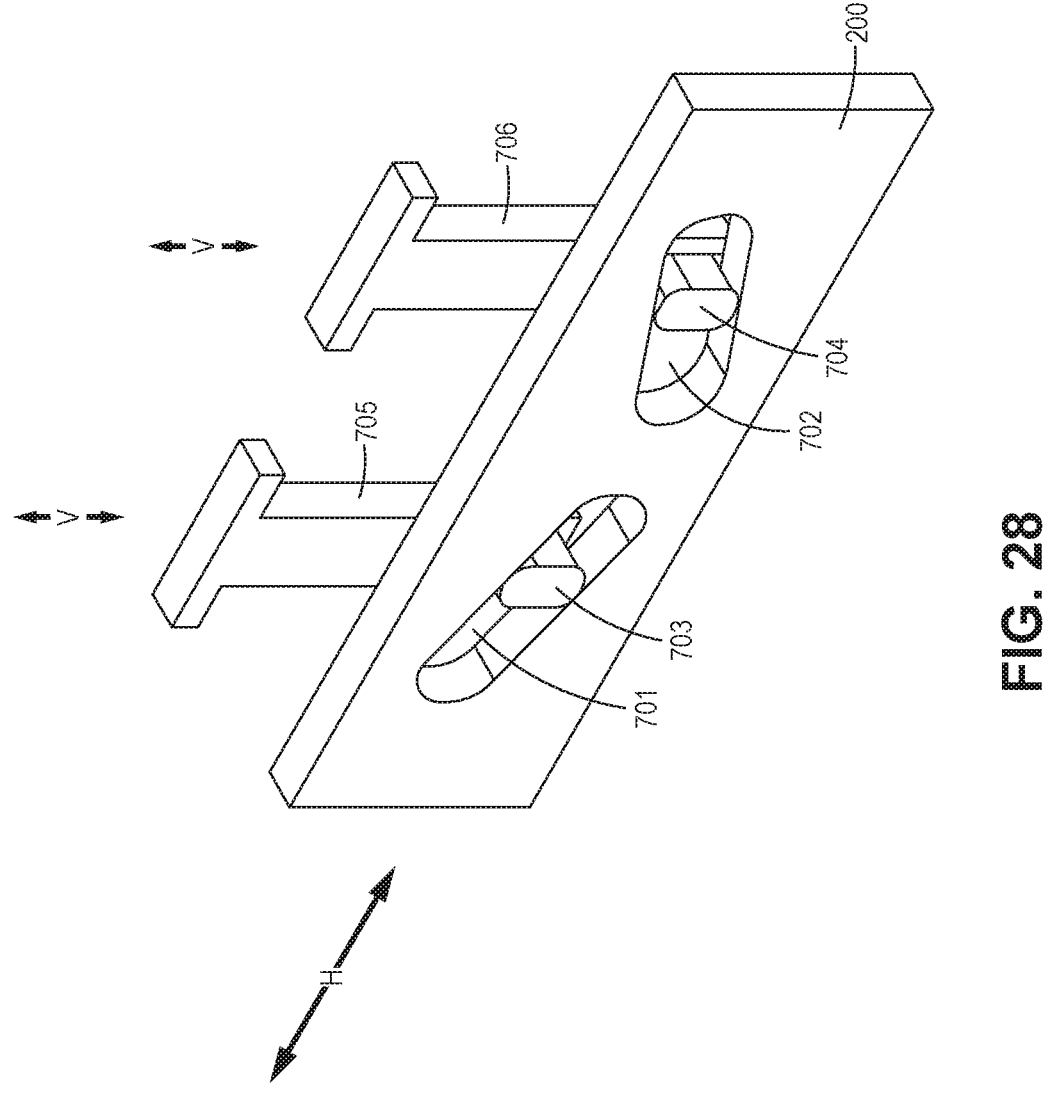

In FIG. 28, the rocker comprises a plate 700 that is connected to the actuator and thus presents two oblong holes 701 and 702 that are of opposing inclination and in which at least two lugs 703 and 704 slide that are respectively connected to actuation members via the rods 705 and 706 respectively, the inclinations of the oblong holes 701 and 702 being closer to the horizontal direction than to the vertical direction. With respect to the orientation in the figure, when the actuator situated on the left pushes the plate 700 to the right, the rod 705 moves up while the rod 706 moves down, and when the actuator pushes the plate 700 to the left, the rod 706 moves up while the rod 705 moves down.

Figure 29:
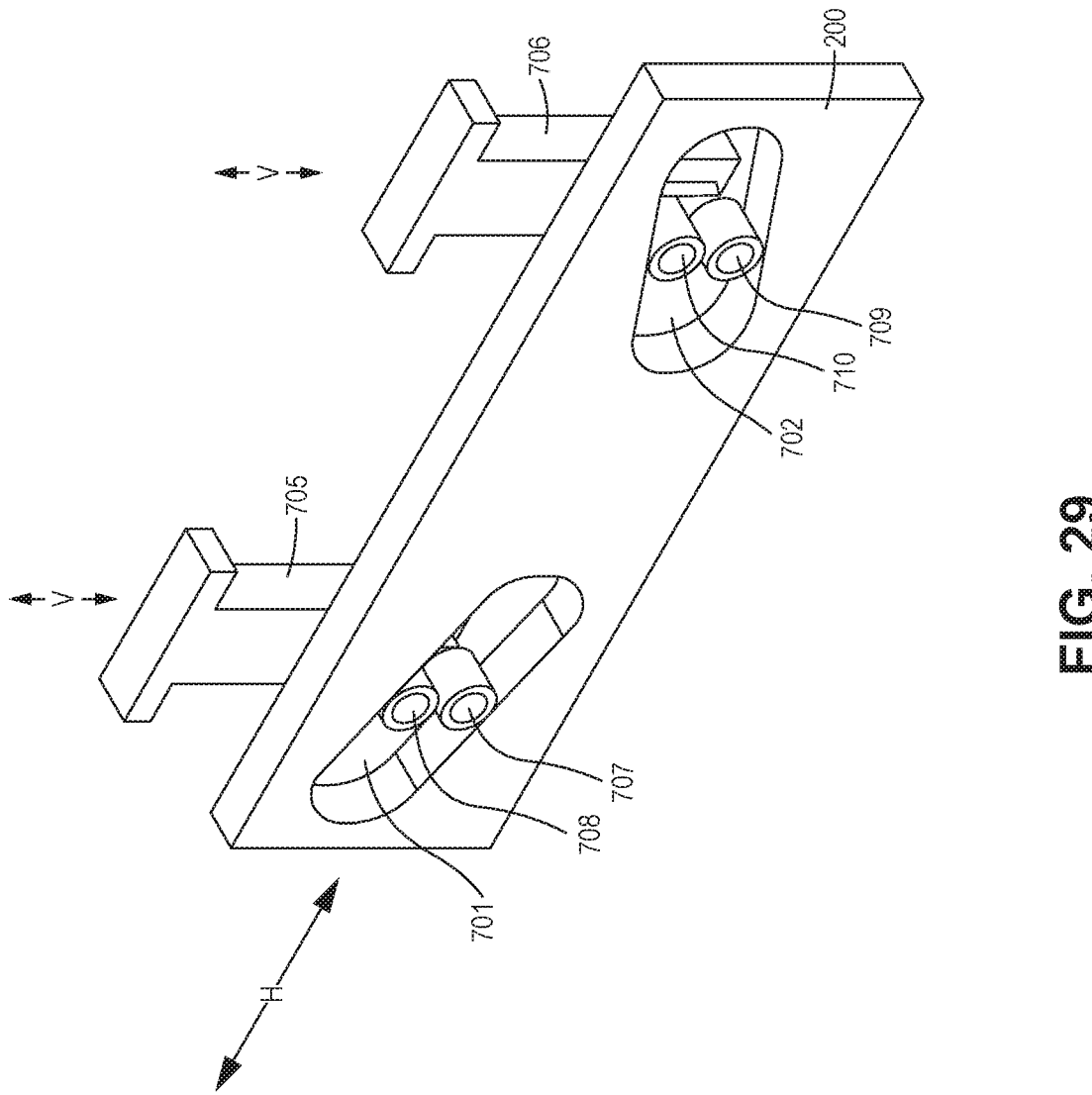

In FIG. 29, the rocker comprises a plate 700 that is connected to the actuator and that presents two oblong holes 701 and 702 of opposing inclination in which at least two pairs of rollers slide, the first pair of rollers 707 and 708 and the second pair of rollers 709 and 710 being respectively connected to the actuation members via the respective rods 705 and 706, the inclinations of the oblong holes 701 and 702 being closer to the horizontal direction than to the vertical direction. With respect to the orientation of the figure, when the actuator situated on the left pushes the plate 700 to the right, the rod 705 moves up while the rod 706 moves down, and when the actuator pushes the plate 700 to the left, the rod 706 moves up while the rod 705 moves down.

Figure 30:
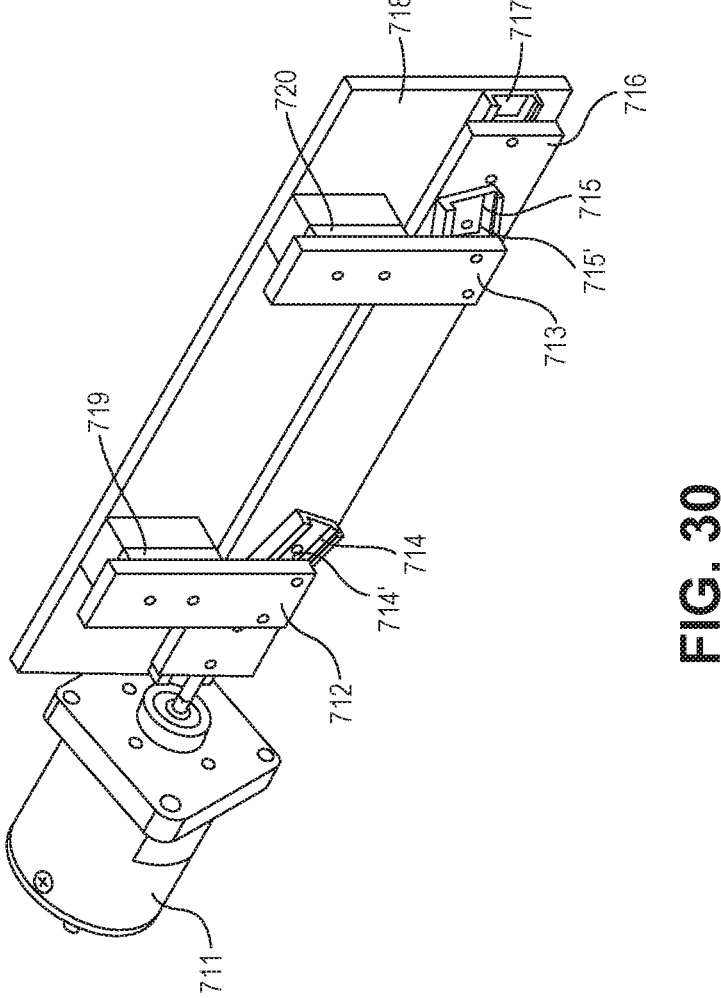

In FIG. 30, the rocker comprises a plate 716 that is connected to the actuator 711 and that presents two inclined oblique rails 714 and 715 of opposing inclination, in which there slide at least two slides 714' and 715' respectively connected to the actuation members, the inclinations of the rails 714 and 715 being closer to the horizontal direction than to the vertical direction. The two rails 714 and 715 are in the same plane parallel to the plane formed by the horizontal direction and by the vertical direction. With respect to the orientation of the figure, when the actuator 711 situated on the left pushes the plate 716 to the right, which slides in the rail 717 fastened to the base block 718, the rod 712 moves up while the rod 713 moves down, the rods 712 and 713 being guided vertically by respective guides 719 and 720, and when the actuator 711 pushes the plate 716 to the left, the rod 713 moves up while the rod 712 moves down.

Figure 31:
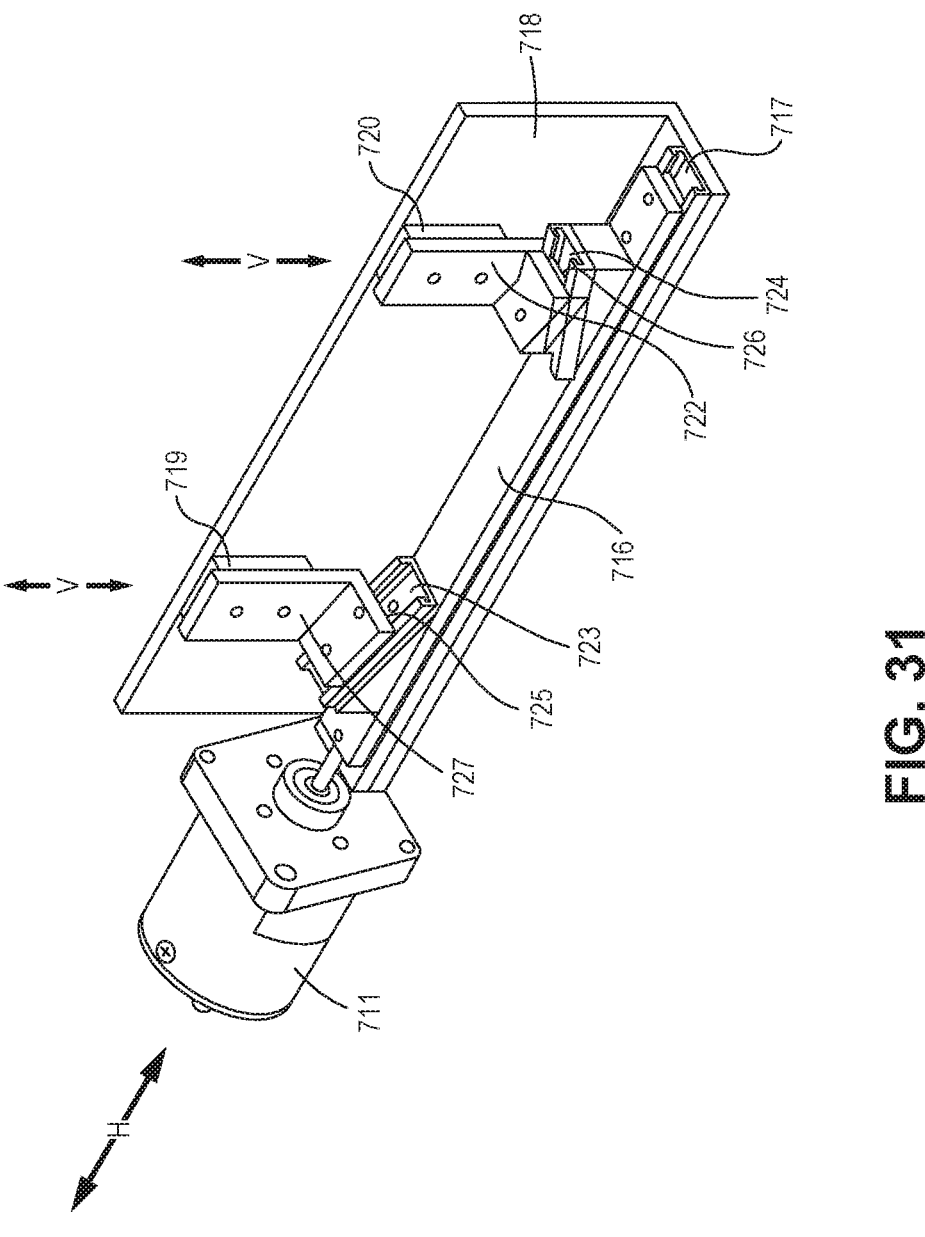

In FIG. 31, the rocker comprises a plate 716 that is connected to the actuator 711 and that presents two inclined oblique rails 723 and 724 of opposing inclination, in which there slide at least two slides 725 and 726 that are respectively connected to the actuation members, the inclinations of the rails 723 and 724 being closer to the horizontal direction than to the vertical direction. The two rails 723 and 724 are in two distinct planes perpendicular to the plane formed by the horizontal direction and by the vertical direction. With respect to the orientation of the figure, when the actuator 711 situated on the left pushes the plate 716 to the right, which plate slides in the rail 717 fastened to the base block 718, the rod 721 moves up while the rod 722 moves down, the rods 721 and 722 being guided vertically by the respective guides 719 and 720, and when the actuator 711 pushes the plate 716 to the left, the rod 722 moves up while the rod 721 moves down. Each of the rods 721 and 722 is essentially constituted by two mutually orthogonal portions.

Figure 32:
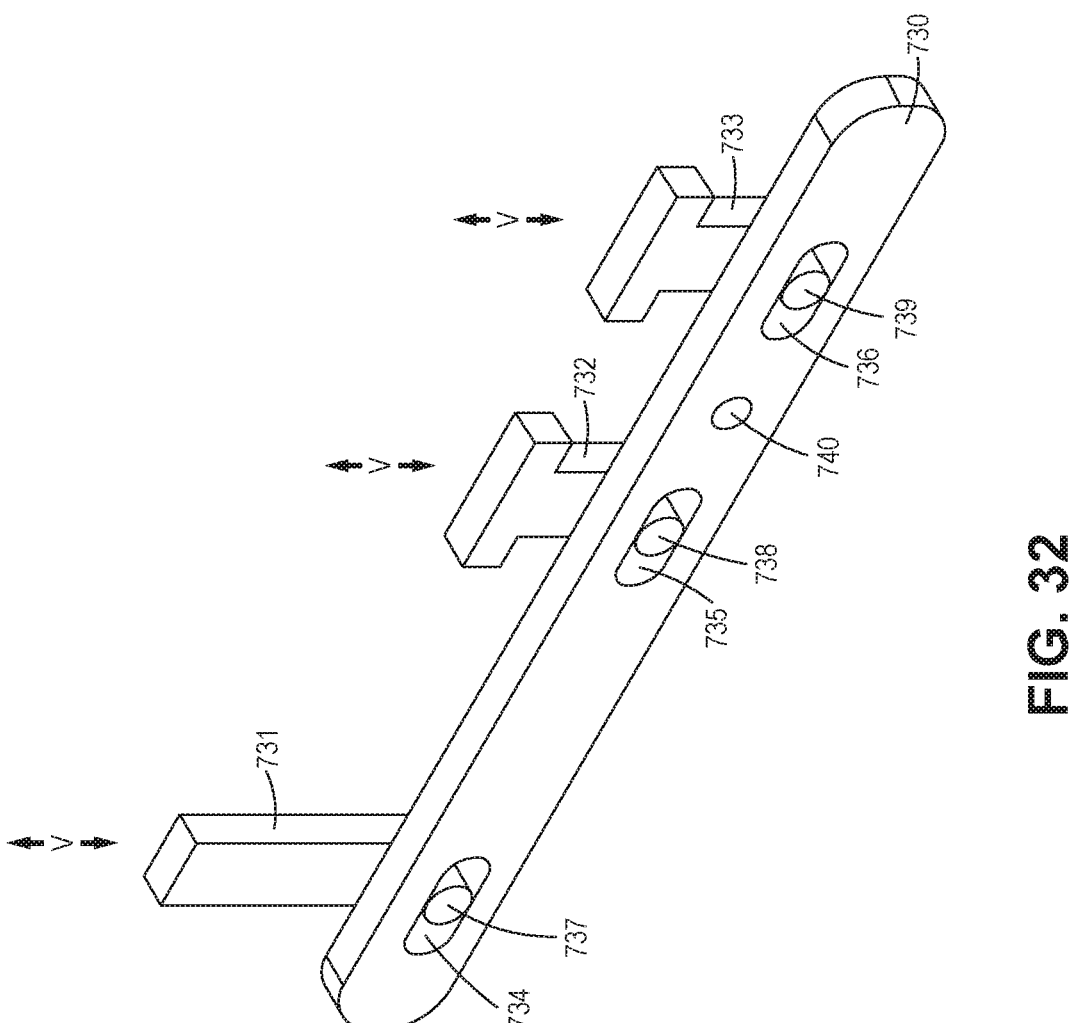

In FIG. 32, the rocker is mounted to pivot about an axis 740 and comprises a plate 730 that is connected to the actuator and that presents three oblique rails 734, 735, and 736, that all have the same inclination and in which there slide at least three lugs 737, 738, and 739, that are respectively connected to the actuator and to the actuation members, the inclinations of the oblong holes 734, 735, and 736 being closer to the horizontal direction than to the vertical direction, two of the oblong holes 735 and 736 being arranged symmetrically about the pivot axis 740 and receiving the lugs 738 and 739 that are connected respectively to the two actuation members, the third oblong hole 734 being arranged further away from the pivot axis 740 than the two oblong holes 738 and 739 that are connected to the actuation members and it receives the lugs 737 that is connected to the actuator. When the rod 731 of the actuator moves down, the rod 732 of the first actuation member moves down, while the rod 733 of the second actuation member moves up. When the rod 731 of the actuator moves up, the rod 732 of the first actuation member moves up while the rod 733 of the second actuation member moves down.

Figure 33:
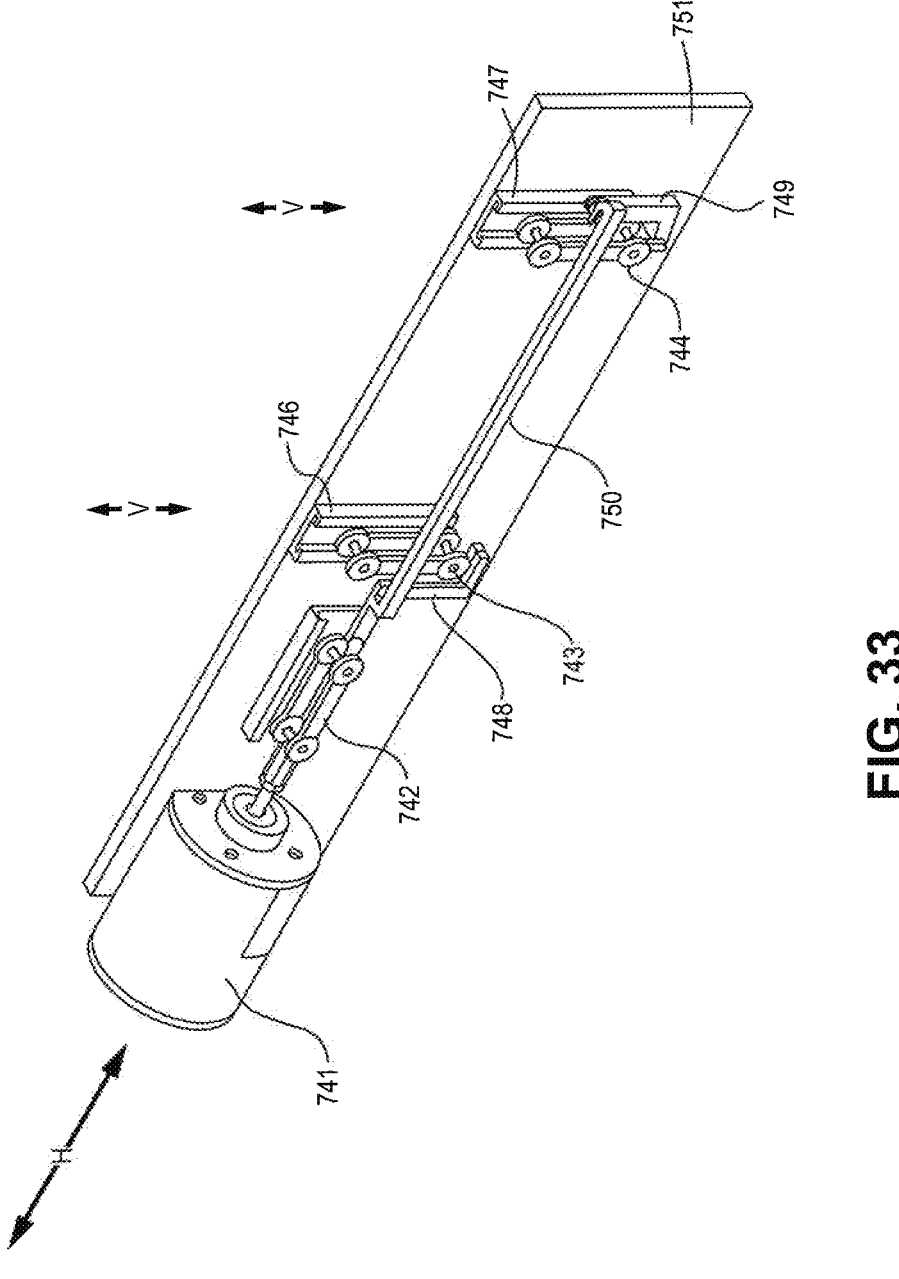

In FIG. 33, the rocker comprises a plate 751 that is connected to the actuator 741 and that presents two connecting rod and crankshaft systems 743 & 748 and 744 & 749 in which the crankshafts 748 and 749 are L-shaped and oriented in opposite directions, the small portion of the L-shape of each crankshaft 748 and 749 extending substantially in the horizontal direction and the large portion of the L-shape of the crankshaft 748 and 749 extending substantially in the vertical direction. The connecting rods 743 and 744 are connected respectively to the two actuation members. With respect to the orientation of the figure, when the actuator 741 situated on the left pushes the connecting rod 742, itself actuating the bar 750 that causes the L-shaped crankshafts 748 and 749 to rock at the bends of their L-shapes, the connecting rod 743 moves up in the rail 746 fastened to the plate 751, while the connecting rod 744 moves down in the rail 747 fastened to the plate 751. Conversely, when the actuator 741 situated on the left pulls the connecting rod 742, itself actuating the strip 750 that causes the L-shaped crankshafts 748 and 749 to rock at the bends of their L-shapes, the connecting rod 743 moves down in the rail 746 fastened on a plate 751, while the connecting rod 744 moves up in the rail 747 fastened to the plate 751.

Figure 34:
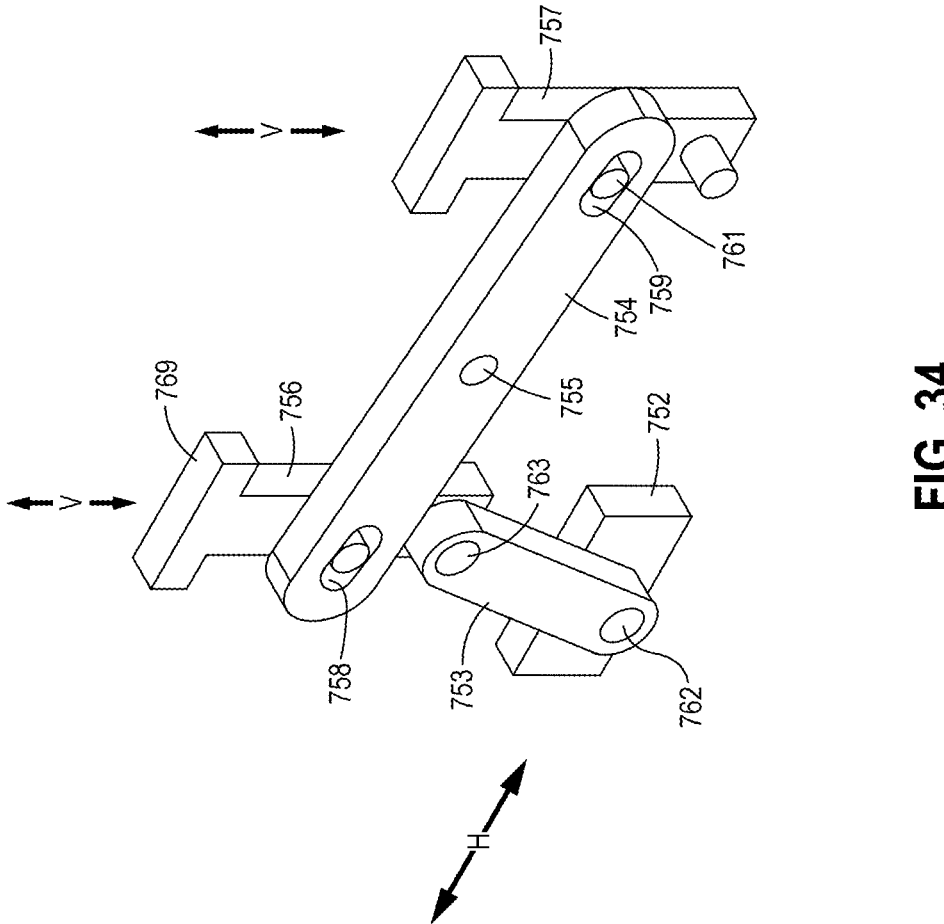

In FIG. 34, the rocker comprises plate 752 that is connected at one side to the actuator and that is connected at the other side to a first end 762 of the connecting rod 753 having its second end 763 connected to a first end 763 of a first rod 756 sliding at its middle 760 in a first oblong hole 758 situated at a first end of a bar 754 that pivots at its middle 755 with its second end presenting a second oblong hole 759 in which there slides the middle 761 of a second rod 757, the oblong holes 758 and 759 being parallel to the bar 754, the second end 764 and 765 of the two rods 756 and 757 being connected respectively to the actuation members. With respect to the orientation of the figure, when the actuator, which situated on the left, pushes the plate 752, the connecting rod 753 causes the first rod 756 to move up, thereby rocking the bar 754 about its pivot axis 755 in a clockwise direction, thus causing the second rod 757 to move down. Conversely, when the actuator, situated on the left, pulls the plate 752, the connecting rod 753 moves the first rod 756 down, thereby rocking the bar 754 about its pivot axis 755 in the counterclockwise direction, thereby causing the second rod 757 to rise.

Figure 35:
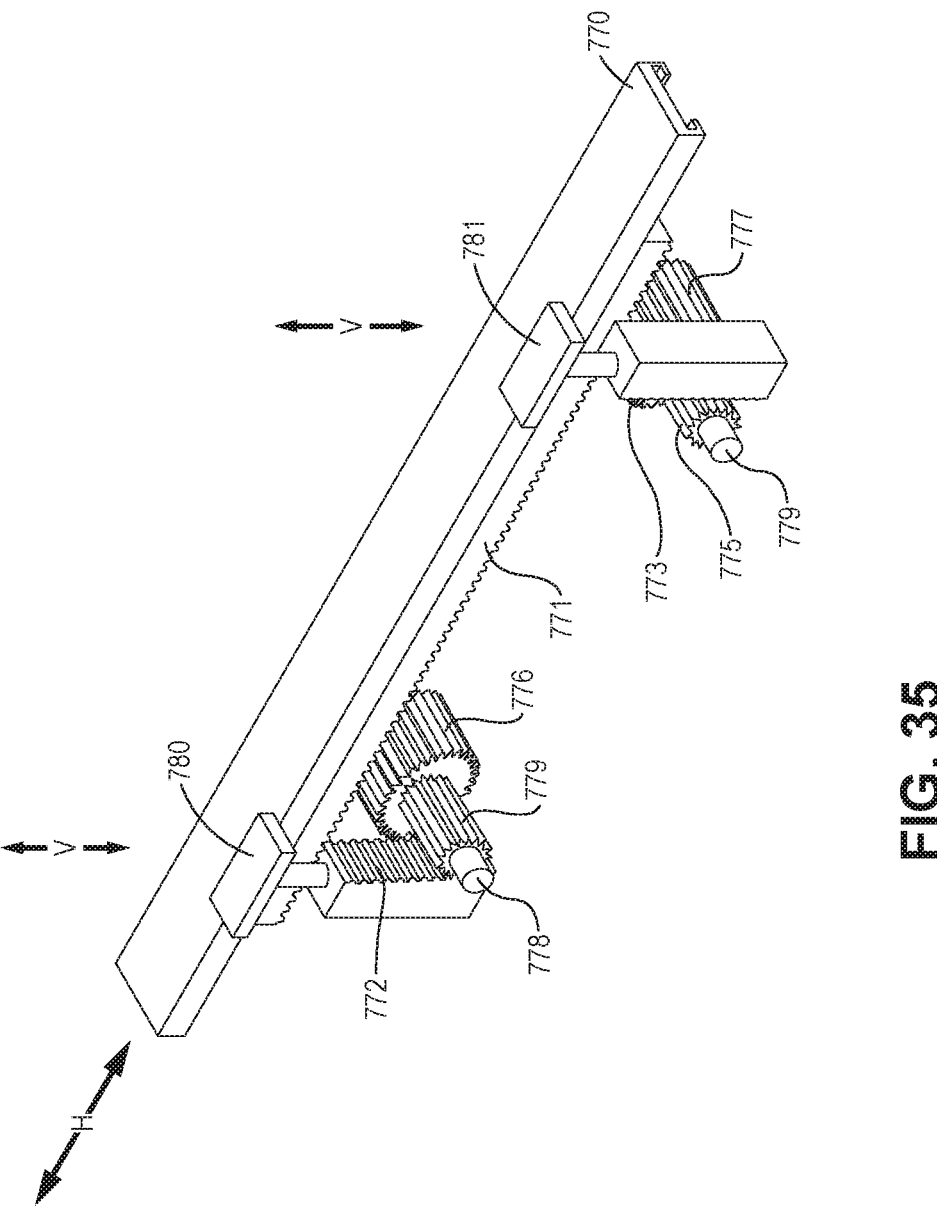

In FIG. 35, the rocker comprises a plate 770 that is connected to the actuator and that presents a first rack 771 in the horizontal direction, two second racks 772 and 773 that are connected respectively to the actuation members and that extend in the vertical direction with their toothed portions facing each other, and two gear systems situated between the first rack 771 and respective ones of the two second racks 772 and 773, each of the gear systems comprising a large gear 776 or 777 meshing with the first rack 771, and a small gear 774 or 775 meshing with a respective one of the second racks 772 or 773. The large gear 776 and the small gear 774 lie on the same axis 778. The large gear 777 and the small gear 775 lie on the same axis 779. With respect to the orientation of the figure, when the actuator situated on the left pushes the plate 770, thus pushing the first rack 771 to the right, it causes the large gears 776 and 777 to turn clockwise, thereby also turning the two small gears 774 and 775 clockwise, thus causing the second rack 772 to move up and the second rack 773 to move down, consequently actuating upward movement of the rod 780 and downward movement of the rod 781, the two rods 780 and 781 being connected to respective ones of the actuation members. Conversely, when the actuator, situated on the left, pulls the plate 770, thus pulling the first rack 771 to the left, it causes the large gears 776 and 777 to turn counterclockwise, also causing the small gears 774 and 775 to turn counterclockwise, and thus causing the second rack 772 to move down and the second rack 773 to move up, thereby consequently causing the rod 780 to move down and the rod 781 to move up.

The invention claimed is:

1. A robotized module for actuating an elongated flexible medical device comprising:
   a base,
   a pair of actuation members each having an actuation surface, the pair of actuation members being suitable for being placed alternately in an actuation configuration wherein the actuation surfaces of the actuation members of the pair of actuation members are engaged with the elongated flexible medical device to be actuated and arranged on either side thereof, and in a free configuration wherein the actuation surface of the actuation members of the pair of actuation members is not engaged with the elongated flexible medical device,
   the pair of actuation devices being movably mounted with respect to the base according to a degree of freedom between a first and a second positions,
   a control member suitable for controlling in a cyclically repeated manner a movement with respect to the base of the actuation members of the pair of actuation members in the actuation configuration from the first to the second position, thus actuating the elongated flexible medical device with respect to the base, and a movement with respect to the base of the actuation members of the pair of actuation members in the free configuration from the second to the first position without actuating the elongated flexible medical device with respect to the base,
   wherein the movement with respect to the base of the actuation members from the first position to the second position comprises at least:
   a translation of the actuation members with respect to the base along a transverse direction to the local longitudinal direction of the elongated flexible medical device and in the same direction,
   wherein the degree of freedom between the first and second positions is a first degree of freedom, wherein the pair of actuation members is also movably mounted with respect to the base according to a second degree of freedom differing from the first degree of freedom between the first and a third positions,
   the control member being suitable for controlling in a cyclically repeated manner a movement with respect to the base of the actuation members in the actuation configuration from the first to the third position, thus actuating the elongated flexible medical device with respect to the base, and a movement with respect to the base of the actuation members in the free configuration from the third to the first position without actuating the elongated flexible medical device with respect to the base,
   wherein the control member controls in a cyclically repeated manner a movement with respect to the base of the actuation members, so as to generate translation of the elongated flexible medical device over a stroke in the first direction along the longitudinal direction, by cyclically repeating in controlled manner the following steps:

first step: the free configuration enters the actuation configuration, by both actuation members moving in opposite directions along the transverse direction, second step: in the actuation configuration, simultaneous movement of the actuation members is generated in the same direction along the longitudinal direction in a first direction, thereby generating an identical movement of the elongated flexible medical device, third step: in order to pass from the actuation configuration to the free configuration, the two actuation members are caused to move in opposite directions along the transverse direction, in the direction opposite to the direction used for passing the actuation members from the free configuration to the actuation configuration, fourth step: in the free configuration, optionally simultaneous movement in the same direction of the actuation members is generated in the longitudinal direction in a second direction opposite to the first direction, thereby not generating a movement of the elongated flexible medical device, thereby returning to the free configuration of said first step, at same location as in said first step, and wherein the translation of the actuation members with respect to the base along the transverse direction to the local longitudinal direction of the elongated flexible medical device and in opposite directions is suitable rolling of the elongated flexible medical device on the actuation surfaces about the local longitudinal direction of the elongated flexible medical device.

2. The robotized module according to claim 1, wherein the movement of the actuation members from the first position to the second position with respect to the base comprises a combination of:

a translation of the actuation members with respect to the base along a parallel direction to a local longitudinal direction of the elongated flexible medical device, and/or a translation of the actuation members with respect to the base along a transverse direction to a local longitudinal direction of the elongated flexible medical device and in opposite directions, and/or the translation of the actuation members with respect to the base along the transverse direction to a local longitudinal direction of the elongated flexible medical device, said translation being performed in the same direction for both actuation members, and/or a translation of the actuation members with respect to the base along a transverse direction to a local longitudinal direction of the elongated flexible medical device and in the same direction.

3. The robotized actuation module according to claim 2, wherein the base is a first base, the pair of actuation members is a first pair of actuation members, the robotized module further comprising:

a second base, a second pair of actuation members each having an actuation surface, the second pair of actuation members being suitable for being placed alternately in an actuation configuration wherein the actuation surfaces of the actuation members of the second pair of actuation members are engaged with the elongated flexible medical device to be actuated and arranged on either side thereof, and in a free configuration wherein the actuation surface of the actuation members of the second pair of actuation members is not engaged with the elongated flexible medical device, the second pair of actuation members being movably mounted with respect to the second base according to a degree of freedom between a first and a second positions, the control member being further suitable for controlling in a cyclically repeated manner a movement with respect to the base of the actuation members of the second pair of actuation members in the actuation configuration from the first to the second position, thus actuating the elongated flexible medical device with respect to the second base, and a movement with respect to the second base of the actuation members of the second pair of actuation members in the free configuration from the second to the first position without actuating the elongated flexible medical device with respect to the second base.

4. The robotized method for actuating a catheter and/or a guide, controlling the set of actuation members of a robotized module according to claim 2 and comprising:

a first operating mode wherein the set of actuation members moves in translation the guide and/or the catheter, a second operating mode wherein the set of actuation members rotates the guide and/or the catheter about itself, characterized in that the method also comprises:

a third operating mode wherein:

the set of actuation members moves, simultaneously, in translation the guide and rotates, alternately in one direction and in the other direction, the guide about itself, and/or, the set of actuation members moves, simultaneously, in translation the catheter and rotates, alternately in one direction and in the other direction, the catheter about itself.

5. The robotized method for actuating a catheter and/or a guide, according to claim 4, characterized in that:

in the third operating mode, the set of actuation members moves, simultaneously, in translation the guide and/or the catheter according to the variations of the control of a man-machine interface and automatically rotates the guide and/or the catheter about itself alternately in one direction and in the other direction.

6. The robotized method for actuating a catheter and/or a guide, according to claim 5, characterized in that:

in the third operating mode, the set of actuation members moves, simultaneously, in translation the guide and/or the catheter according to the variations of the control of a man-machine interface and automatically rotates the guide and/or the catheter about itself alternately in one direction and in the other direction, the alternating rotational frequency being proportional to the translation speed.

7. The robotized module according to claim 1, wherein the degree of freedom between the first and second positions is a first degree of freedom, wherein the pair of actuation members is also movably mounted with respect to the base according to a second degree of freedom differing from the first degree of freedom between the first and a third positions, the control member being suitable for controlling in a cyclically repeated manner a movement with respect to the base of the actuation members in the actuation configuration from the first to the third position, thus actuating the elongated flexible medical device with respect to the base, and a movement with respect to the base of the actuation members in the free configuration from the third to the first position without actuating the elongated flexible medical device with respect to the base.

8. The robotized module according to claim 7, wherein the movement with respect to the base of the actuation members from the first position to the second position and the movement with respect to the base of the actuation members from the first to the third position comprise two distinct combinations from:

a translation of the actuation members with respect to the base along a parallel direction to the local longitudinal direction of the elongated flexible medical device, a translation of the actuation members with respect to the base along a transverse direction to the local longitudinal direction of the elongated flexible medical device and in opposite directions, the translation of the actuation members with respect to the base along the transverse direction to the local longitudinal direction of the elongated flexible medical device, said translation being performed in the same direction for both actuation members, a translation of the actuation members with respect to the base along a transverse direction to the local longitudinal direction of the elongated flexible medical device and in the same direction.

9. The robotized actuation module according to claim 1, wherein the pair of actuation members is suitable for being placed from the free configuration thereof to the actuation configuration thereof by a relative movement of the actuation members with respect to the base, and preferably wherein the first and second positions define the first degree of freedom, wherein the pair of actuation members is also movably mounted with respect to the base according to a third degree of freedom from the free configuration thereof to the actuation configuration thereof.

10. The robotized actuation module according to claim 1, wherein the base is a first base, the pair of actuation members is a first pair of actuation members, the robotized module further comprising:

a second base, a second pair of actuation members each having an actuation surface, the second pair of actuation members being suitable for being placed alternately in an actuation configuration wherein the actuation surfaces of the actuation members of the second pair of actuation members are engaged with the elongated flexible medical device to be actuated and arranged on either side thereof, and in a free configuration wherein the actuation surface of the actuation members of the second pair of actuation members is not engaged with the elongated flexible medical device, the second pair of actuation members being movably mounted with respect to the second base according to a degree of freedom between a first and a second positions, the control member being further suitable for controlling in a cyclically repeated manner a movement with respect to the base of the actuation members of the second pair of actuation members in the actuation configuration from the first to the second position, thus actuating the elongated flexible medical device with respect to the second base, and a movement with respect to the second base of the actuation members of the second pair of actuation members in the free configuration from the second to the first position without actuating the elongated flexible medical device with respect to the second base.

11. The robotized actuation module according to claim 10, wherein the first base and the second base are rigidly connected or a common base.

12. The robotized actuation module according to claim 9, wherein the control member is suitable for controlling the movements of the actuation members of the first pair and of the second pair in a synchronized manner.

13. The robotized actuation module according to claim 12, wherein the control member is suitable for placing the actuation members of the first pair and of the second pair simultaneously in the actuation configuration, and/or wherein the control member is suitable for placing the actuation members of the first pair and of the second pair simultaneously in the free configuration, and/or wherein the control member is suitable for placing simultaneously the actuation members of the first pair and of the second pair in one case in the actuation configuration and in the other in the free configuration.

14. The robotized module for actuating a movable element in the form of an elongated flexible medical device according to claim 1, characterized in that it comprises a movement transmission chain comprising:

a base block of a member for actuating a movable element, three actuators controlling the block of the actuation member respectively along three mutually distinct translation directions, via three respective interfaces with the base block of the actuation member, and in that the intersection of the mean surface areas of the three interfaces is located in the central region of the base block of the actuation member.

15. The robotized module for actuating the movable element in the form of the elongated flexible medical device according to claim 14, characterized in that:

the three interfaces are substantially plane, these three interfaces are orthogonal with respect to one another, and these three interfaces are interlocked in one another.

16. The robotized actuation module according to claim 1, characterized in that it also comprises at least:

an actuator controlling the pair of actuation members, an intermediate part transmitting the movement of the actuator to the pair of actuation members, so as to translate in opposite directions the two actuation members of the pair of actuation members, while keeping the distance between the two actuation members of the pair of actuation members substantially constant, so as to rotate the elongated flexible medical device about itself when said device is arranged between the two actuation members of the pair of actuation members.

17. The robotized actuation module according to claim 16, characterized in that:

the intermediate part is a rocker converting the translation of the actuator along a first direction into two translations in opposite directions of the two respective actuation members along a second orthogonal direction to the first direction.

18. The robotized actuation module according to claim 17, characterized in that:

the rocker comprises a plate which is connected to the actuator and which has two inclined oblong holes of opposing inclination wherein at least two lugs respectively connected to the pair of actuation members slide, the inclination of the oblong holes being closer to the first direction than the second direction.

19. The robotized actuation module according to claim 17, characterized in that:

the rocker comprises a plate which is connected to the actuator and which has two inclined oblong holes of opposing inclination wherein at least two rollers respectively connected to the pair of actuation members slide, the inclination of the oblong holes being closer to the first direction than the second direction.

20. The robotized actuation module according to claim 17, characterized in that:

the rocker comprises a plate which is connected to the actuator and which has two inclined oblique rails of opposing inclination wherein at least two slides respectively connected to the pair of actuation members slide, the inclination of the rails being closer to the first direction than the second direction.

21. The robotized actuation module according to claim 20, characterized in that:

the two rails are in the same plane parallel to the plane formed by the first direction and by the second direction.

22. The robotized actuation module according to claim 20, characterized in that:

the two rails are in two distinct planes perpendicular to the plane formed by the first direction and by the second direction.

23. The robotized actuation module according to claim 17, characterized in that:

the rocker is pivoting about an axis and comprises a plate which is connected to the actuator and which has inclined oblong holes of the same inclination wherein at least three lugs or three roller respectively connected to the actuator and to the actuation members slide, the inclination of the oblong holes being closer to the first direction than the second direction, two of the oblong holes being arranged symmetrically with respect to the pivoting axis and receiving the lugs or the rollers respectively connected to the two actuation members, the third oblong hole being arranged further from the pivoting axis than the two oblong holes connected to the actuation members and receiving the lug or the roller connected to the actuator.

24. The robotized actuation module according to claim 17, characterized in that:

the rocker comprises a plate which is connected to the actuator and which has two connecting rod and L-shaped crankshaft systems, the two L-shaped crankshafts being oriented in opposite directions, the small part of the L of the crankshafts being substantially along a first direction, the large part of the L of the crankshafts being substantially along the second direction.

25. The robotized actuation module according to claim 17, characterized in that:

the rocker comprises a plate which is connected on one side to the actuator and which is connected on an other side to a first end of a connecting rod a second end whereof is connected to a first end of a first rod sliding at a center thereof in a first oblong hole situated at a first end of a bar pivoting at the center thereof and the second end whereof has a second oblong hole wherein the center of a second rod slides, the oblong holes being parallel to the bar the second ends of the two rods being respectively connected to the actuation members.

26. The robotized actuation module according to claim 17, characterized in that:

the rocker comprises a plate which is connected to the actuator and which has a first rack along the first direction, two second racks which are respectively connected to the actuation members and which are along the second direction and the toothed parts whereof face one another, two gear systems situated between the first rack and the respective two second racks, each of the gear systems comprising a large gear engaging with the first rack and a small gear engaging with one of the second racks.

27. The robotized method for actuating a catheter and/or a guide, controlling the set of actuation members of a robotized module according to claim 1 and comprising:

a first operating mode wherein the set of actuation members moves in translation the guide and/or the catheter, a second operating mode wherein the set of actuation members rotates the guide and/or the catheter about itself, characterized in that the method also comprises:

a third operating mode wherein:

the set of actual s moves, simultaneously, in translation the guide and rotates, alternately in one direction and in the other direction, the guide about itself, and/or, the set of actuation members moves, simultaneously, in translation the catheter and rotates, alternately in one direction and in the other direction, the catheter about itself.

* * * * *